(12) United States Patent
Luo et al.

(10) Patent No.: US 8,946,436 B2
(45) Date of Patent: Feb. 3, 2015

(54) OXAZOLIDINONE COMPOUNDS AND THEIR USES IN PREPARATION OF ANTIBIOTICS

(75) Inventors: Youfu Luo, Wuhou District Chengdu (CN); Zhenling Wang, Wuhou District Chengdu (CN); Yuquan Wei, Wuhou District Chengdu (CN); Funeng Geng, Mianyang (CN)

(73) Assignees: Sichuan Gooddoctor Pharmaceutical Group Co., Ltd. (CN); Si Chuan University (CN)

( * ) Notice: Subject to any disclaimer, the term of this patent is extended or adjusted under 35 U.S.C. 154(b) by 0 days.

(21) Appl. No.: 14/126,999

(22) PCT Filed: Jun. 15, 2012

(86) PCT No.: PCT/CN2012/076982
§ 371 (c)(1),
(2), (4) Date: Dec. 17, 2013

(87) PCT Pub. No.: WO2012/171479
PCT Pub. Date: Dec. 20, 2012

(65) Prior Publication Data
US 2014/0142144 A1    May 22, 2014

(30) Foreign Application Priority Data
Jun. 17, 2011 (CN) .......................... 2011 1 0164375

(51) Int. Cl.
*C07D 401/00* (2006.01)
*C07D 413/10* (2006.01)
*C07D 413/14* (2006.01)
*C07D 401/04* (2006.01)

(52) U.S. Cl.
CPC ............ *C07D 413/10* (2013.01); *C07D 413/14* (2013.01); *C07D 401/04* (2013.01)
USPC ...................................................... 546/275.4

(58) Field of Classification Search
CPC ...................................................... C07D 401/04
USPC ...................................................... 546/275.4
See application file for complete search history.

(56) References Cited

FOREIGN PATENT DOCUMENTS

CN    1172484    2/1998
WO    2008143649 A2    11/2008

OTHER PUBLICATIONS

Kwon et al. Bull. Korean Chem. Soc. 2009, vol. 30, No. 8 1895-1898.*
International Search Report for corresponding appliction PCT/CN2012/076982 filed Jun. 15, 2012; Mail date Sep. 6, 2012.
J.S. Kwon, "Synthesis and Biological Evaluation of Novel Substituted Pyrrolyl and Pyrazolyl Oxazolidinone Analougues", BULL. Korean Chemistry, Soc. 2009, vol. 30, No. 8, pp. 1895-1898.
Zou, Cui et al, "Quantitative structure-activity relationship of oxazolidinone compounds", West China Journal of Pharmaceutical Sciences, 2007, vol. 22, No. 3, pp. 255-258.
European Search Report for European Application No. 12800130.2; Application Filing Date Jun. 15, 2012; Date of Report Oct. 10, 2014, 5 pages.
Genin et al., "Substituent effects on the antibacterial activity of nitrogen-carbon-linked (azolylphenyl)oxazolidinones with expanded activity against the fastidious gram-negative organisms *Haemophilus influenza* and *Moraxella catarrhalis*", J. Med. Chem. (2000) 43: 953-970.

* cited by examiner

Primary Examiner — Nizal Chandrakumar
(74) Attorney, Agent, or Firm — Cantor Colburn LLP

(57) ABSTRACT

The invention belongs to the field of medicaments, and particularly relates to oxazolidinone compounds and their uses in the preparation of antibiotics. A technical problem to be solved by the invention is to provide new oxazolidinone compounds having the structure represented by Formula I. The oxazolidinone compounds of the invention, which are new compounds obtained through numerous screening, have significant antibacterial activity against bacteria such as drug-resistant *staphylococcus aureus*, fecal coliform bacteria, and *streptococcus pneumoniae*, while exhibiting low toxicity. The invention provides new options for the development and application of antibiotics.

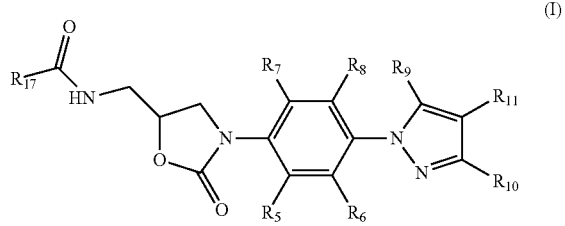

13 Claims, 1 Drawing Sheet

OXAZOLIDINONE COMPOUNDS AND THEIR USES IN PREPARATION OF ANTIBIOTICS

FIELD OF THE INVENTION

The invention belongs to the field of medicaments, and particularly relates to oxazolidinone compounds and their uses in the preparation of antibiotics.

BACKGROUND OF THE INVENTION

The discovery and application of antibiotics was one of the greatest achievements in the field of medicaments in the 20th century, which can be regarded as a revolutionary discovery in the process of fighting against diseases. From then on, medical field entered a golden age for significant reduction in the incidence rate of bacterial diseases. However, due to the extensive use and even abuse of antibiotics, the efficacy thereof is weakening as the drug resistance of bacteria is becoming increasingly serious, and thus the "Age of Post-Antibiotics" is coming closer. A number of new drug-resistant strains have been found clinically, among which MRSA (methicillin-resistant *staphylococcus aureus*), VRE (vancomycin-resistant *enterococci*), PRSP (penicillin-resistant *streptococcus pneumoniae*), and the like have made the clinical treatment rather difficult, because there are only a few kinds of therapeutic medicines against them.

Linezolid is an oxazolidinone compound that was put into the market in the United States in 2000. In clinic, Linezolid is mainly utilized to treat nosocomial pneumonia, soft tissue infections, etc., and is also useful in cure of surgical infectious diseases. In addition, Linezolid displays excellent pharmacokinetic characteristics such as high tissue drug concentration in skeleton, lung, cerebrospinal fluid, etc., and exhibits excellent permeability into infectious bacteria cells. There continues to be interest in discovering and developing novel oxazolidinone medicine candidates.

SUMMARY OF THE INVENTION

The first technical problem to be addressed in the invention is to provide novel oxazolidinone compounds having the structure represented by Formula VI:

Formula VI

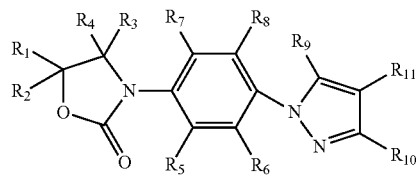

wherein:
$R_1$ is

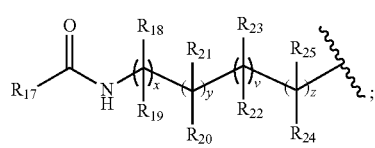

$R_2$ to $R_4$ are each independently H or $C_1$-$C_8$ alkyl;
$R_5$ to $R_8$ are each independently H, F, Cl, Br or $C_1$-$C_8$ alkyl;
$R_9$, $R_{10}$ and $R_{11}$ are each independently H, $C_1$-$C_8$ alkyl,

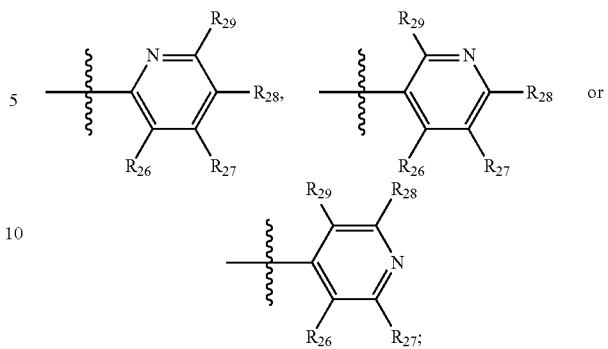

$R_{17}$ is H or $C_1$-$C_8$ alkyl;
$R_{18}$ to $R_{29}$ are each independently H or $C_1$-$C_8$ alkyl; and
v=1 to 2, x=0 to 2, y=0 to 2, and z=0 to 2.

Specifically, when v=1, x=y=z=0, $R_{22}$ and $R_{23}$ are both H, the oxazolidinone compounds have the structure represented by Formula I:

Formula I

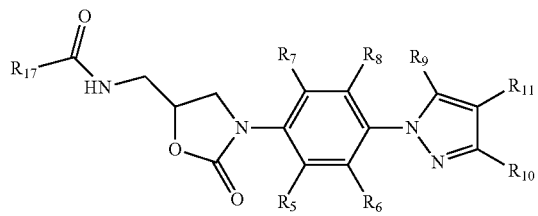

wherein:
$R_5$ to $R_8$ are each independently H, F, Cl, Br or $C_1$-$C_8$ alkyl;
$R_9$, $R_{10}$ and $R_{11}$ are each independently H, substituted phenyl,

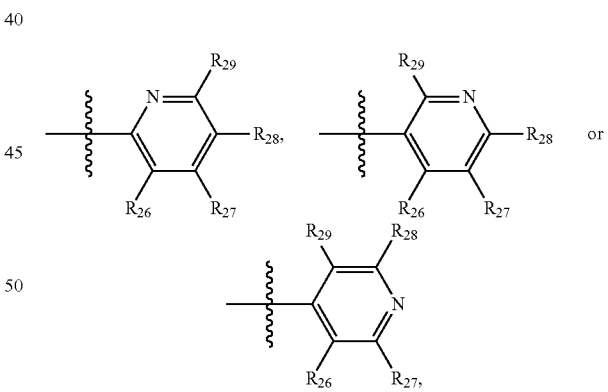

and at least one of $R_9$, $R_{10}$ and $R_{11}$ is not H;
the respective substituents on the substituted phenyl are each independently H, halogen, $C_1$ to $C_4$ alkoxy, $C_1$ to $C_4$ alkyl or $C_1$ to $C_4$ sulfanyl;
$R_{17}$ is H or $C_1$-$C_4$ alkyl; and
$R_{26}$ to $R_{29}$ are each independently H, $C_1$ to $C_4$ alkyl, halogen or carboxyl.

More specifically, among the above-described oxazolidinone compounds, $R_5$ to $R_8$ are each independently H, F, Cl, Br or $C_1$ to $C_4$ alkyl;
$R_9$, $R_{10}$ and $R_{11}$ are each independently H, substituted phenyl,

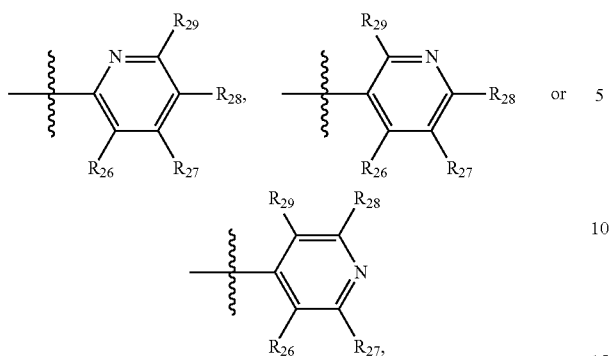

and at least one of $R_9$, $R_{10}$ and $R_{11}$ is not H;

the respective substituents on the substituted phenyl are each independently H, halogen, $C_1$-$C_4$ alkoxy, $C_1$ to $C_4$ alkyl or $C_1$ to $C_4$ sulfanyl;

$R_{17}$ is H or $C_1$ to $C_4$ alkyl; and $R_{26}$ to $R_{29}$ are each independently H, $C_1$ to $C_4$ alkyl, halogen or carboxyl.

Preferably, $R_5$ to $R_8$ are each independently H, F, Cl, Br or $C_1$-$C_4$ alkyl;

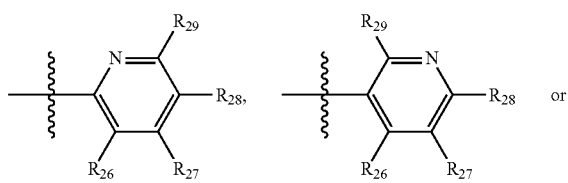

and at least one of $R_9$, $R_{10}$ and $R_{11}$ is not H;

the respective substituents on the substituted phenyl are each independently H, F, Cl, Br, $C_1$-$C_4$ alkoxy, $C_1$-$C_4$ alkyl or $C_1$-$C_4$ sulfanyl;

$R_{17}$ is H or $C_1$-$C_4$ alkyl; and $R_{26}$ to $R_{29}$ are each independently H, $C_1$-$C_4$ alkyl, halogen or carboxyl.

Preferably, $R_5$ to $R_8$ are each independently H, F, Cl or Br;

$R_9$, $R_{10}$ and $R_{11}$ are each independently H, substituted phenyl,

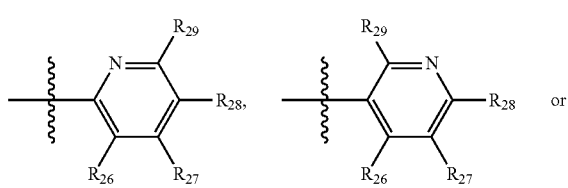

-continued

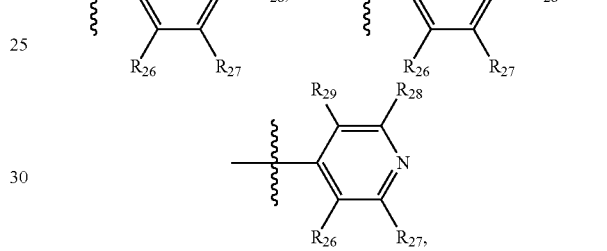

and at least one of $R_9$, $R_{10}$ and $R_{11}$ is not H;

the respective substituents on the substituted phenyl are each independently H, F, Cl, Br, $C_1$-$C_4$ alkoxy, $C_1$-$C_4$ alkyl or $C_1$-$C_4$ sulfanyl;

$R_{17}$ is H or $C_1$-$C_4$ alkyl; and $R_{26}$ to $R_{29}$ are each independently H, F, Cl, Br or carboxyl.

Preferably, $R_5$ to $R_8$ are each independently H, F or Cl;

$R_9$, $R_{10}$ and $R_{11}$ are each independently H, substituted phenyl,

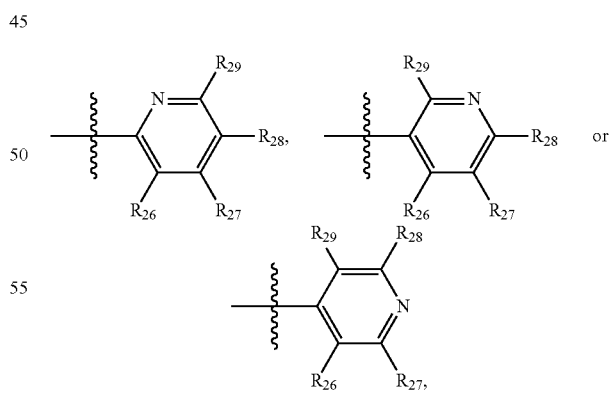

and at least one of $R_9$, $R_{10}$ and $R_{11}$ is not H;

the respective substituents on the substituted phenyl are each independently H, F, Cl, Br, $C_1$-$C_4$ alkoxy, $C_1$-$C_4$ alkyl or $C_1$-$C_4$ sulfanyl;

$R_{17}$ is $C_1$-$C_4$ alkyl; and $R_{26}$ to $R_{29}$ are each independently H, $C_1$-$C_4$ alkyl, F, Cl, Br or carboxyl.

Preferably, $R_5$ to $R_8$ are each independently H or F;

$R_9$, $R_{10}$ and $R_{11}$ are each independently H, substituted phenyl, and at least one of $R_9$, $R_{10}$ and $R_{11}$ is not H;

the substituted phenyl group is substituted by one or two substituents, each independently being H, F, Cl, Br, $C_1$-$C_4$ alkoxy, $C_1$-$C_4$ alkyl, or $C_1$-$C_4$ sulfanyl;

$R_{17}$ is $C_1$-$C_4$ alkyl; and $R_{26}$ to $R_{29}$ are each independently H, $C_1$-$C_4$ alkyl, F, Cl, Br or carboxyl.

Preferably, $R_5$ to $R_8$ are each independently H or F;

$R_9$, $R_{10}$ and $R_{11}$ are each independently H, substituted phenyl,

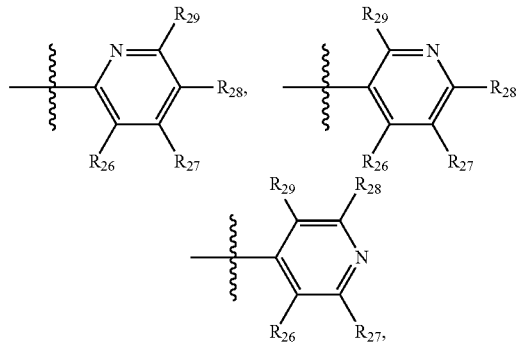

and at least one of $R_9$, $R_{10}$ and $R_{11}$ is not H;

the substituted phenyl is substituted by one or two substituents, each independently being H, Cl, Br, $C_1$-$C_4$ alkoxy, $C_1$-$C_4$ alkyl or $C_1$-$C_4$ sulfanyl;

$R_{17}$ is $C_1$-$C_4$ alkyl; and $R_{26}$ to $R_{29}$ are each independently H, F, Cl, Br or carboxyl;

Preferably, $R_5$ and $R_7$ are H; $R_6$ and $R_8$ are each independently H or F;

$R_9$, $R_{10}$ and $R_{11}$ are each independently H, substituted phenyl,

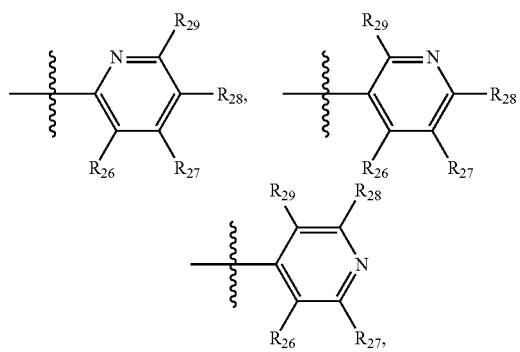

and at least one of $R_9$, $R_{10}$ and $R_{11}$ is not H;

the said substituted phenyl is substituted by one or two substituents, each independently being H, F, Cl, Br, $C_1$-$C_4$ alkoxy, $C_1$-$C_4$ alkyl, or $C_1$-$C_4$ sulfanyl;

$R_{17}$ is $C_1$-$C_4$ alkyl; and $R_{26}$ to $R_{29}$ are each independently H, Br or carboxyl.

Most preferably, $R_5$ and $R_7$ are H; $R_6$ and $R_8$ are each independently H or F;

$R_9$, $R_{10}$ and $R_{11}$ are each independently H,

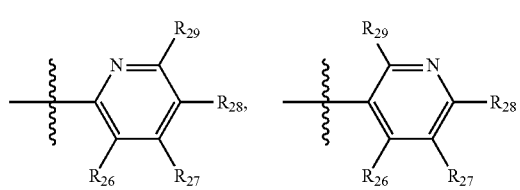

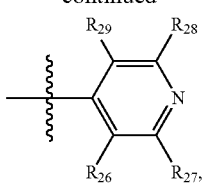

and at least one of $R_9$, $R_{10}$ and $R_{11}$ is not H;

$R_{17}$ is $C_1$-$C_4$ alkyl; and $R_{26}$ to $R_{29}$ are each independently H, Br or carboxyl.

More specifically, in said oxazolidinone compounds:

$R_5$ to $R_8$ are each independently H, F, Cl, Br or $C_1$-$C_8$ alkyl;

$R_9$ and $R_{10}$ are each independently H;

$R_{11}$ is

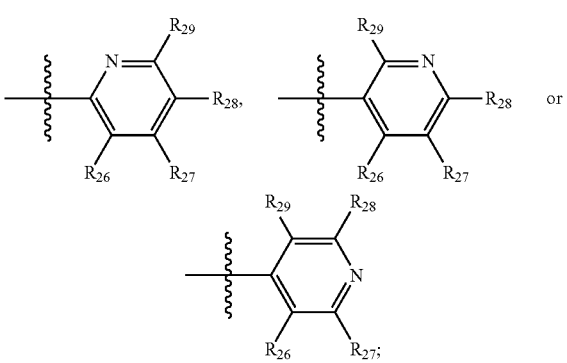

$R_{17}$ is H or $C_1$-$C_4$ alkyl; and $R_{26}$ to $R_{29}$ are H.

Preferably, $R_5$ to $R_8$ are each independently H, F, Cl, Br or $C_1$-$C_4$ alkyl;

$R_9$ and $R_{10}$ are each independently H;

$R_{11}$ is

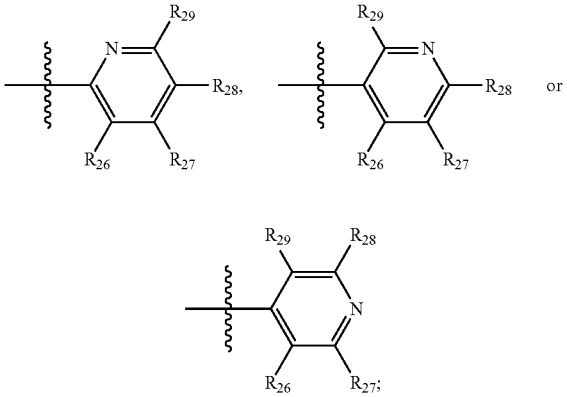

$R_{17}$ is H or $C_1$-$C_4$ alkyl; and $R_{26}$ to $R_{29}$ are H.

Preferably, $R_5$ to $R_8$ are each independently H, F, Cl or Br;

$R_9$ and $R_{10}$ are each independently H;

$R_{11}$ is

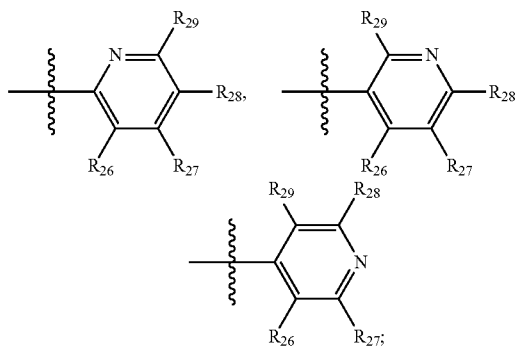

$R_{17}$ is H or $C_1$-$C_4$ alkyl; and
$R_{26}$ to $R_{29}$ are H.
Preferably, $R_5$ to $R_8$ are each independently H, F, Cl or Br;
$R_9$ and $R_{10}$ are each independently H; $R_{11}$ is

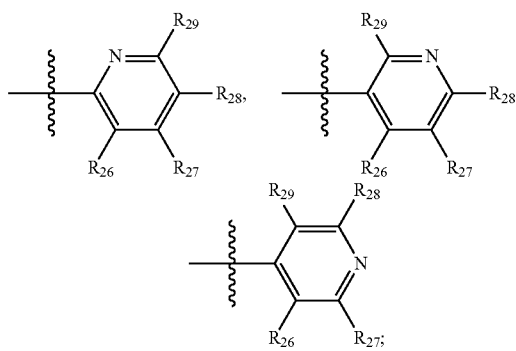

$R_{17}$ is $C_1$-$C_4$ alkyl; and
$R_{26}$ to $R_{29}$ are H.
Preferably, $R_5$ to $R_8$ are each independently H or F;
$R_9$ and $R_{10}$ are each independently H;
$R_{11}$ is

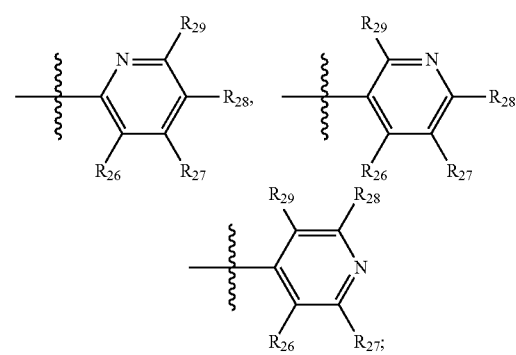

$R_{17}$ is $C_1$-$C_4$ alkyl; and
$R_{26}$ to $R_{29}$ are H.
More preferably, $R_5$ and $R_7$ are H; $R_6$ and $R_8$ are each independently H or F;
$R_9$ and $R_{10}$ are each independently H;

$R_{11}$ is

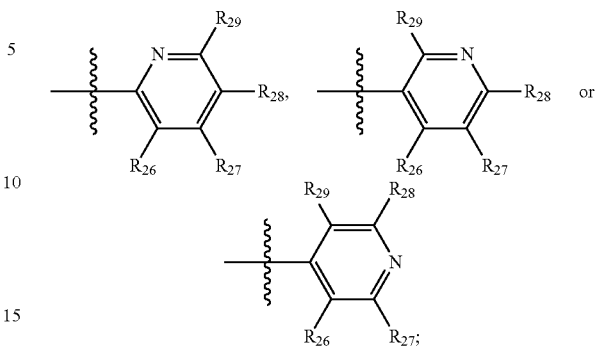

$R_{17}$ is $C_1$-$C_4$ alkyl; and
$R_{26}$ to $R_{29}$ are H.
More specifically, when $R_{17}$ is methyl, the oxazolidinone compounds have the structure represented by Formula II:

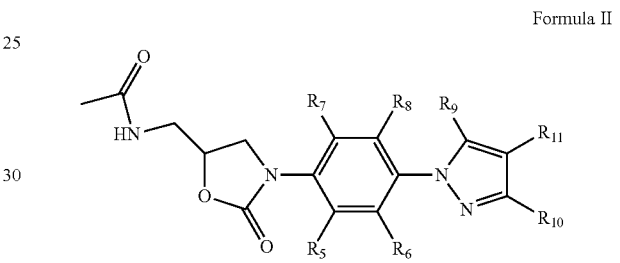

Formula II wherein:
$R_5$ to $R_8$ are each independently H, F, Cl, Br or $C_1$-$C_4$ alkyl;
$R_9$ and $R_{10}$ are each independently H;
$R_{11}$ is

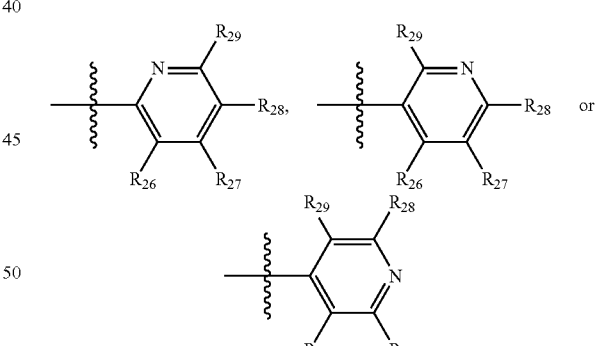

$R_{26}$ to $R_{29}$ are H.
Preferably, $R_5$ to $R_8$ are each independently H, F, Cl or Br;
$R_9$ and $R_{10}$ are each independently H; $R_{11}$ is

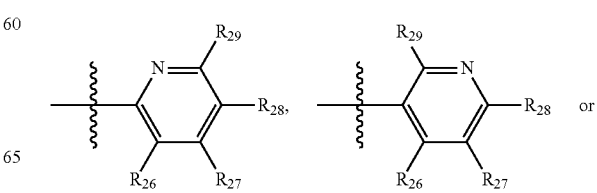

-continued

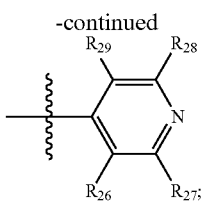

and
$R_{26}$ to $R_{29}$ are H.
Preferably, $R_5$ to $R_8$ are each independently H or F;
$R_9$ and $R_{10}$ are H;
$R_{11}$ is

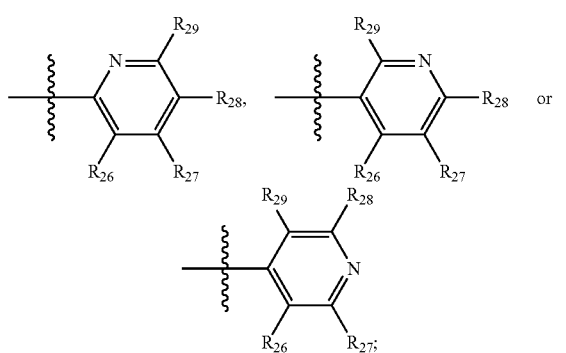

and
$R_{26}$ to $R_{29}$ are H.
Most preferably, $R_5$ and $R_7$ are H; $R_6$ and $R_8$ are each independently H or F;
$R_9$ and $R_{10}$ are H;
$R_{11}$ is

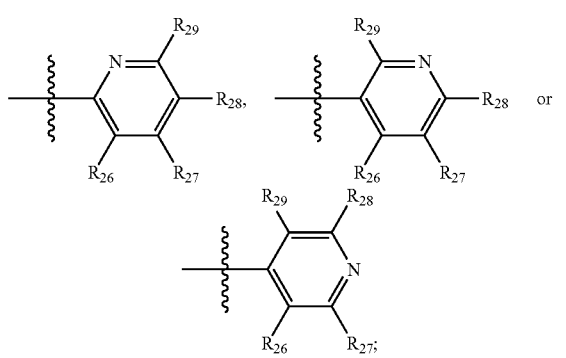

and
$R_{26}$ to $R_{29}$ are H.
Further, when $R_{17}$ is methyl and $R_{11}$ is

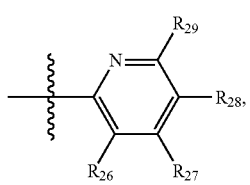

the oxazolidinone compounds have the structure represented by Formula III:

Formula III

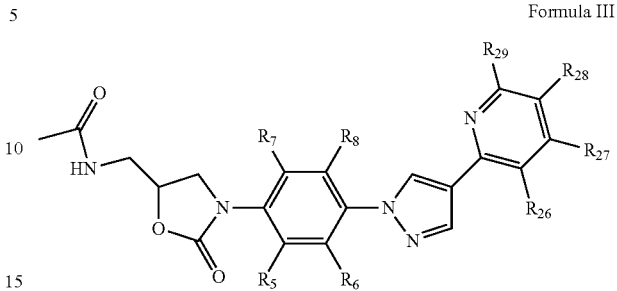

wherein: $R_5$ to $R_8$ are each independently H, F, Cl, Br or $C_1$-$C_4$ alkyl; and
$R_{26}$ to $R_{29}$ are H.
Preferably, $R_5$ to $R_8$ are each independently H, F, Cl or Br; and
$R_{26}$ to $R_{29}$ are H.
More preferably, $R_5$ to $R_8$ are each independently H or F; and
$R_{26}$ to $R_{29}$ are H.
Most preferably, $R_5$ and $R_7$ are H; $R_6$ and $R_8$ are each independently H or F; and
$R_{26}$ to $R_{29}$ are H.
Further, the oxazolidinone compounds have the structure represented by Formula IV:

Formula IV

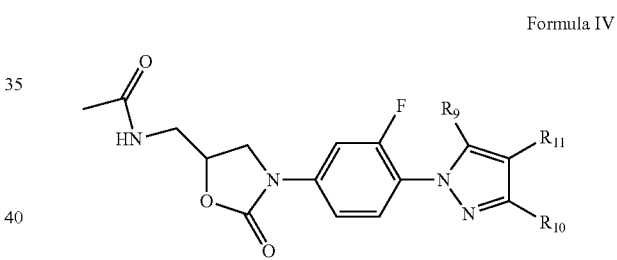

wherein:
$R_9$, $R_{10}$ and $R_{11}$ are each independently H, substituted phenyl,

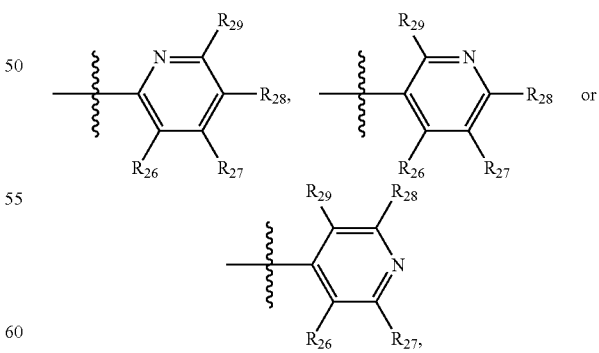

and at least one of $R_9$, $R_{10}$ and $R_{11}$ is not H;
the respective substituents on the substituted phenyl are each independently H, halogen, $C_1$-$C_4$ alkoxy, $C_1$-$C_4$ alkyl or $C_1$-$C_4$ sulfanyl; and
$R_{26}$ to $R_{29}$ are each independently H, $C_1$-$C_4$ alkyl, halogen or carboxyl.

Preferably, $R_9$, $R_{10}$ and $R_{11}$ are each independently H, substituted phenyl,

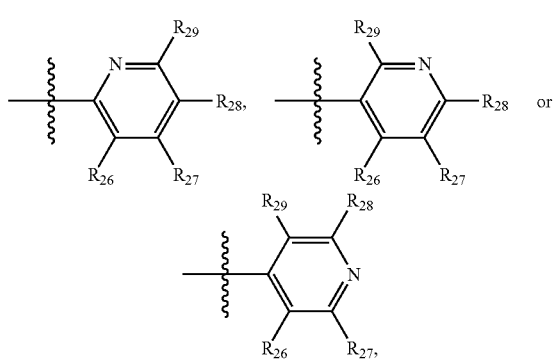

and at least one of $R_9$, $R_{10}$ and $R_{11}$ is not H;
the respective substituents on the substituted phenyl are each independently H, F, Cl, Br, $C_1$-$C_4$ alkoxy, $C_1$-$C_4$ alkyl or $C_1$-$C_4$ sulfanyl; and
$R_{26}$ to $R_{29}$ are each independently H, $C_1$-$C_4$ alkyl, F, Cl, Br or carboxyl.

Preferably, $R_9$, $R_{10}$ and $R_{11}$ are each independently H, substituted phenyl,

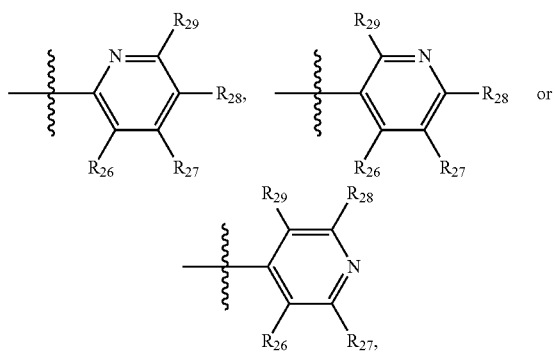

and at least one of $R_9$, $R_{10}$ and $R_{11}$ is not H;
the respective substituents on the substituted phenyl are each independently H, F, Cl, Br, $C_1$-$C_4$ alkoxy, $C_1$-$C_4$ alkyl or $C_1$-$C_4$ sulfanyl; and
$R_{26}$ to $R_{29}$ are each independently H, F, Cl, Br or carboxyl.

Preferably, $R_9$, $R_{10}$ and $R_{11}$ are each independently H, substituted phenyl,

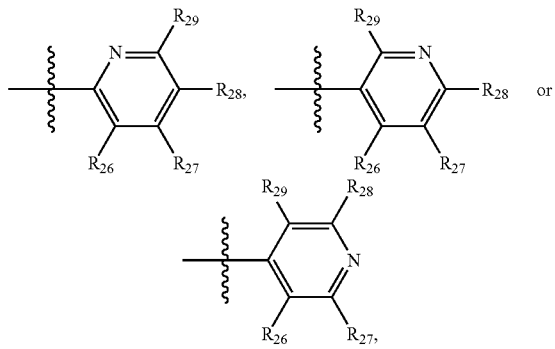

and at least one of $R_9$, $R_{10}$ and $R_{11}$ is not H;
the substituted phenyl is substituted by one or two substituents, each independently being H, Cl, Br, $C_1$-$C_4$ alkoxy, $C_1$-$C_4$ alkyl or $C_1$-$C_4$ sulfanyl; and
$R_{26}$ to $R_{29}$ are each independently H, Cl, Br or carboxyl.

Preferably, $R_9$, $R_{10}$ and $R_{11}$ are each independently H,

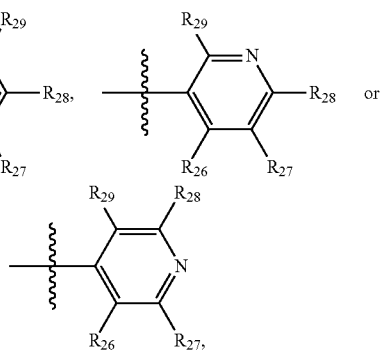

and at least one of $R_9$, $R_{10}$ and $R_{11}$ is not H; and
$R_{26}$ to $R_{29}$ are each independently H, Cl, Br or carboxyl.

Most preferably, $R_9$, $R_{10}$ and $R_{11}$ are each independently H,

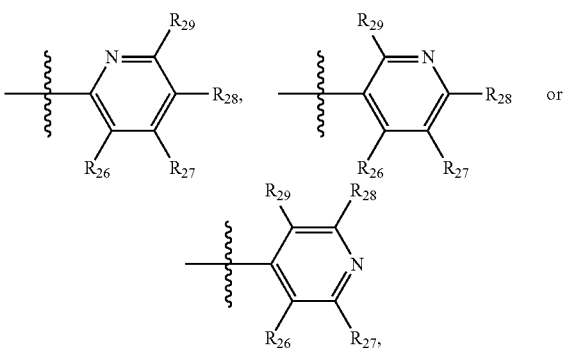

and at least one of $R_9$, $R_{10}$ and $R_{11}$ is not H; and
$R_{26}$ to $R_{29}$ are each independently H, Br or carboxyl.

Further, when $R_9$ and $R_{10}$ are H, the oxazolidinone compounds have the structure represented by Formula V:

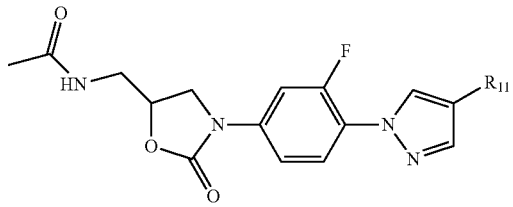

Formula V wherein:
$R_{11}$ is substituted phenyl,

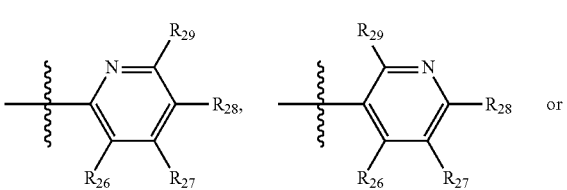

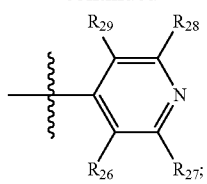

the respective substituents on the substituted phenyl are each independently H, F, Cl, Br, $C_1$-$C_4$ alkoxy, $C_1$-$C_4$ alkyl or $C_1$-$C_4$ sulfanyl; and Preferably, $R_{11}$ is

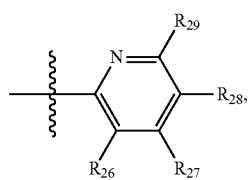 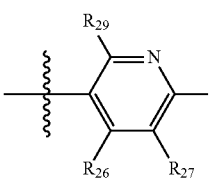 or

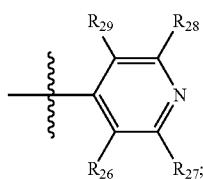

and $R_{26}$ to $R_{29}$ are each independently H, F, Cl, Br or carboxyl.

Preferably, $R_{11}$ is

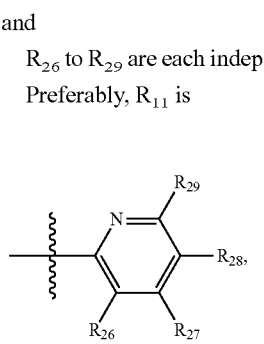 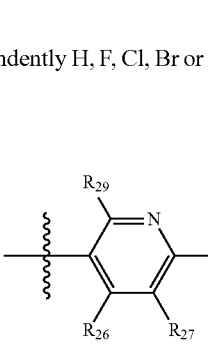 or and $R_{26}$ to $R_{29}$ are each independently H, Cl, Br or carboxyl.

Preferably, $R_{11}$ is

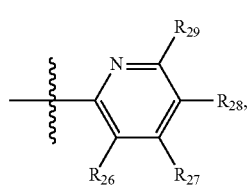 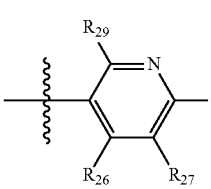 or and $R_{26}$ to $R_{29}$ are each independently H, Br or carboxyl.

Most preferably, $R_{11}$ is

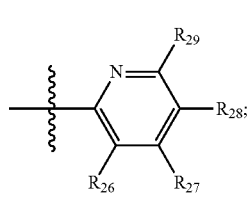

and $R_{26}$ to $R_{29}$ are each independently H.

Further, the structures of the oxazolidinone compounds are as follows:

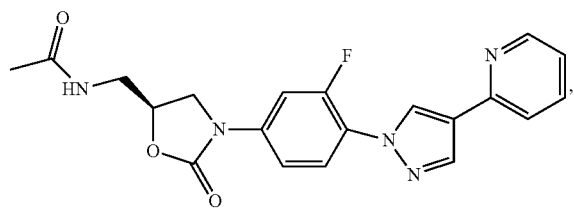

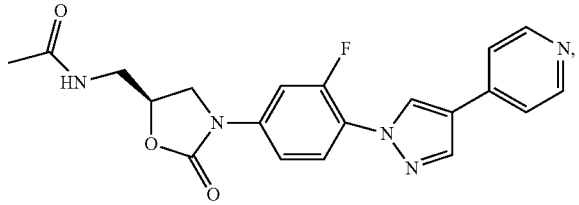

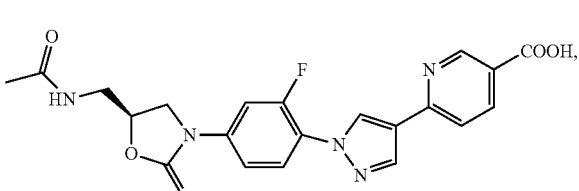

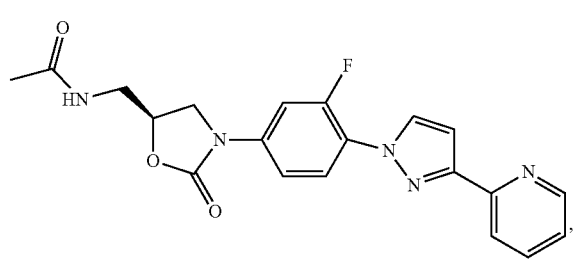

-continued
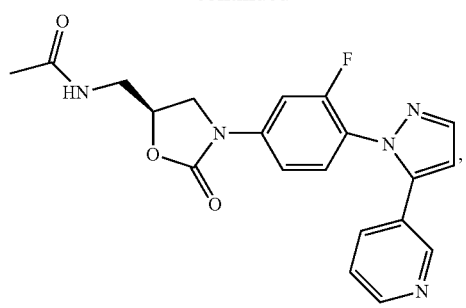
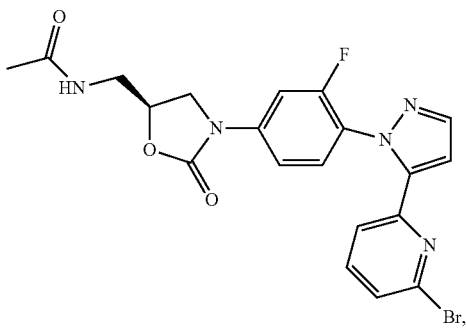
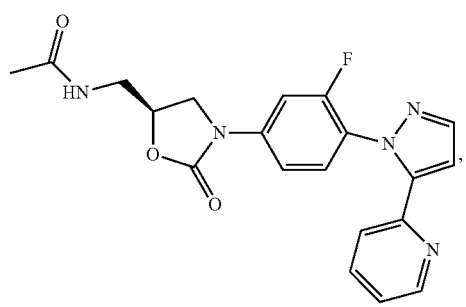 [SMILES: CC(=O)NC[C@H]1CN(c2ccc(-n3nccc3-c3ccccn3)c(F)c2)C(=O)O1]
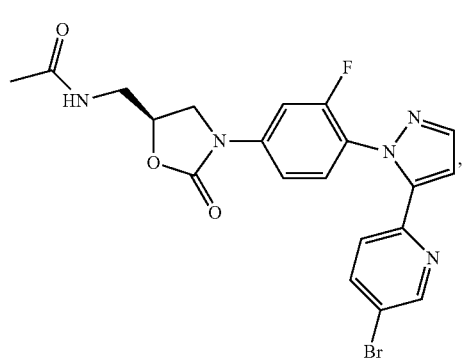
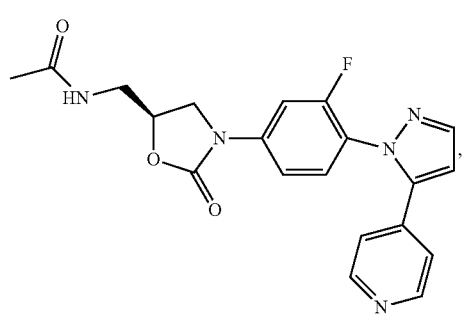
-continued
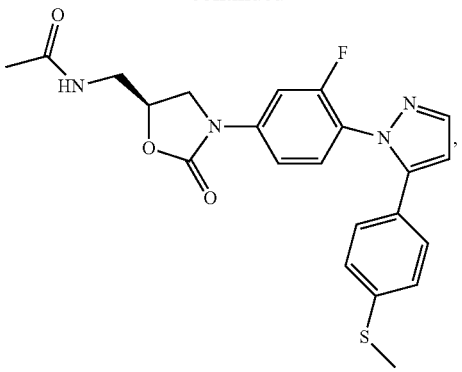
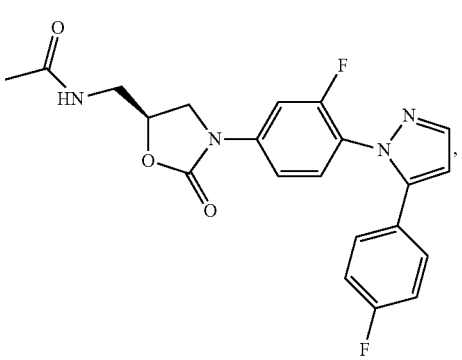
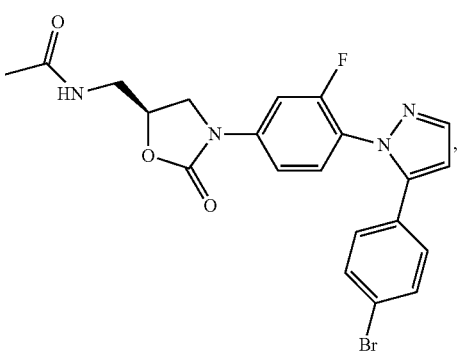
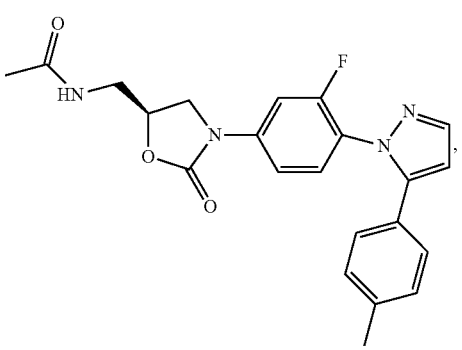

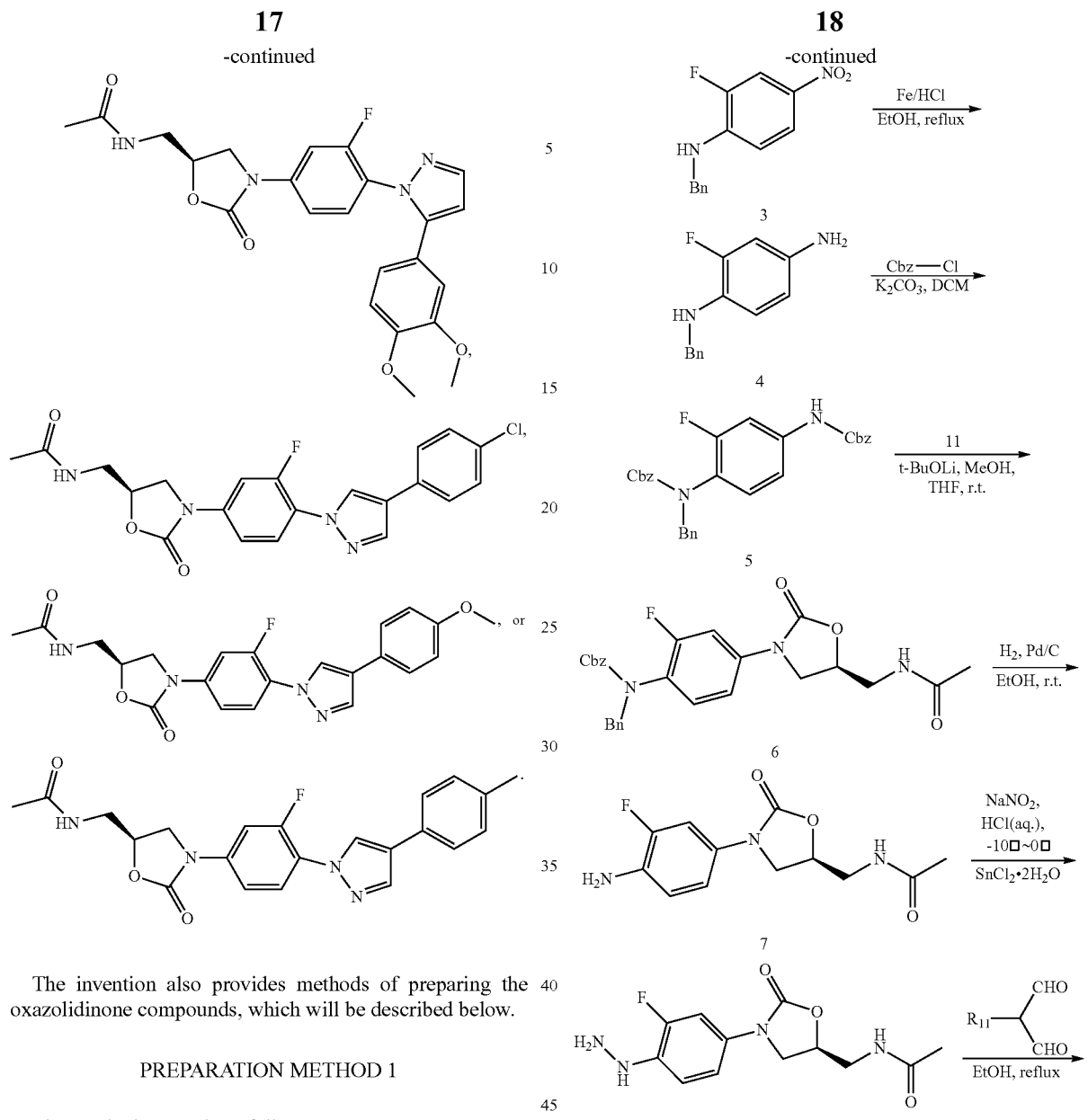
The invention also provides methods of preparing the oxazolidinone compounds, which will be described below.
PREPARATION METHOD 1
The synthetic route is as follows:
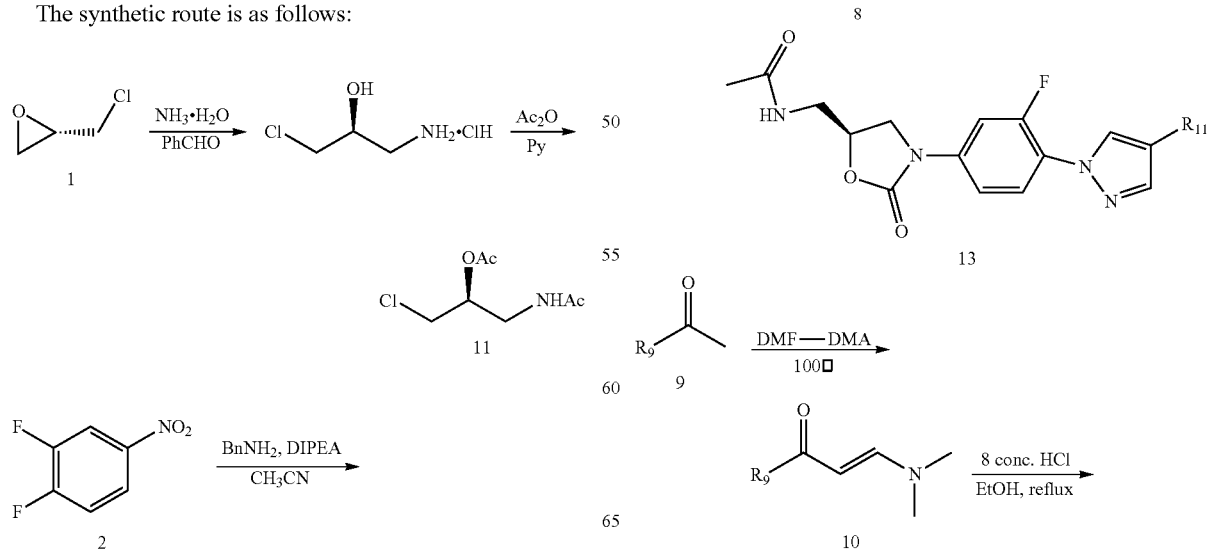

-continued

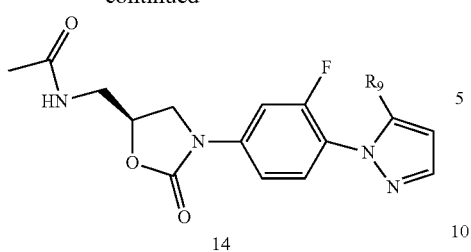

14

The preparation method 1 comprises the following steps:

(1) reacting Compound 1 with benzaldehyde and Ac$_2$O to obtain Compound 11;
(2) reacting Compound 2 with benzylamine to obtain Compound 3;
(3) reducing Compound 3 with Fe powder to obtain Compound 4;
(4) reacting Compound 4 with carbobenzoxy chloride (Cbz-Cl) to obtain Compound 5;
(5) reacting Compound 5 with Compound 11 to obtain Compound 6;
(6) reducing Compound 6 with palladium on carbon (Pd/C) to obtain Compound 7;
(7) reacting Compound 7 with NaNO$_2$ and SnCl$_2$ to obtain Compound 8;
(8) reacting Compound 8 with

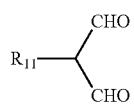

to obtain Product 13;
(9) reacting Compound 9 with N,N-dimethyl formamide dimethyl acetal (DMF-DMA) to obtain Compound 10; and
(10) reacting Compound 10 with Compound 8 to obtain Product 14.

PREPARATION METHOD 2

The synthetic route is as follows:

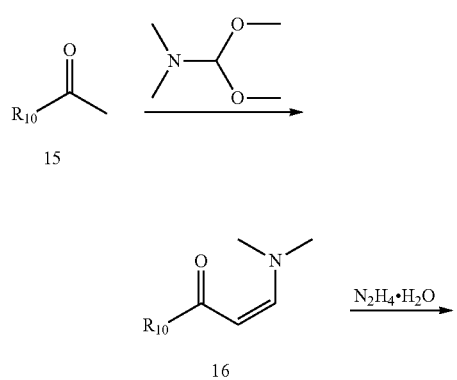

-continued

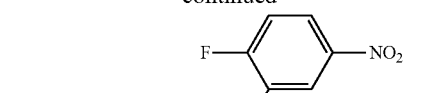

17

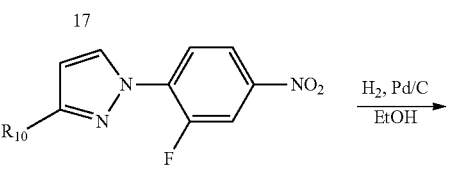

18

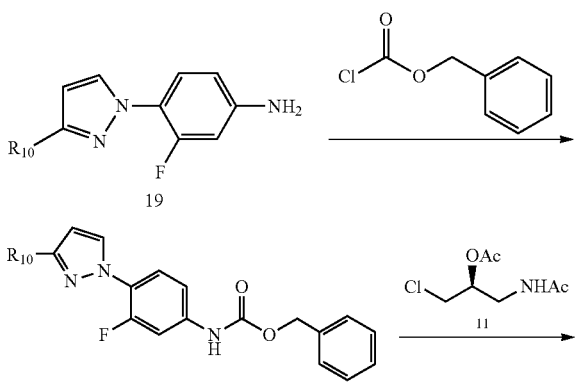

19

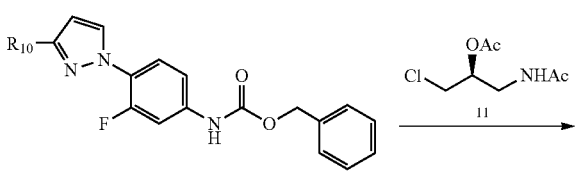

20

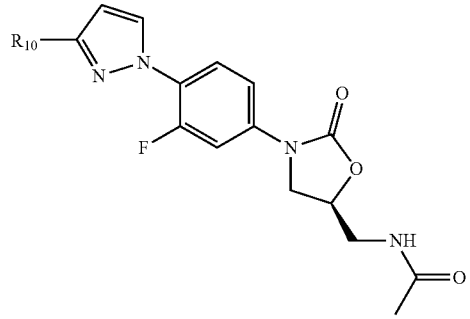

12

The preparation method 2 comprises the following steps:

(1) reacting Compound 15 with N,N-dimethyl formamide dimethyl acetal (DMF-DMA) to obtain Compound 16;
(2) reacting Compound 16 with hydrazine hydrate to obtain Compound 17;
(3) reacting Compound 17 with 3,4-difluoronitrobenzene 2 to obtain Compound 18;
(4) reducing Compound 18 with palladium on carbon (Pd/C) to obtain Compound 19;
(5) reacting Compound 19 with Cbz-Cl to obtain Compound 20; and
(6) Compound 20 undergoing cyclization reaction with Compound 11 in the presence of lithium tert-butoxide (t-BuOLi) to obtain Product 12.

PREPARATION METHOD 3

The synthetic route is as follows:

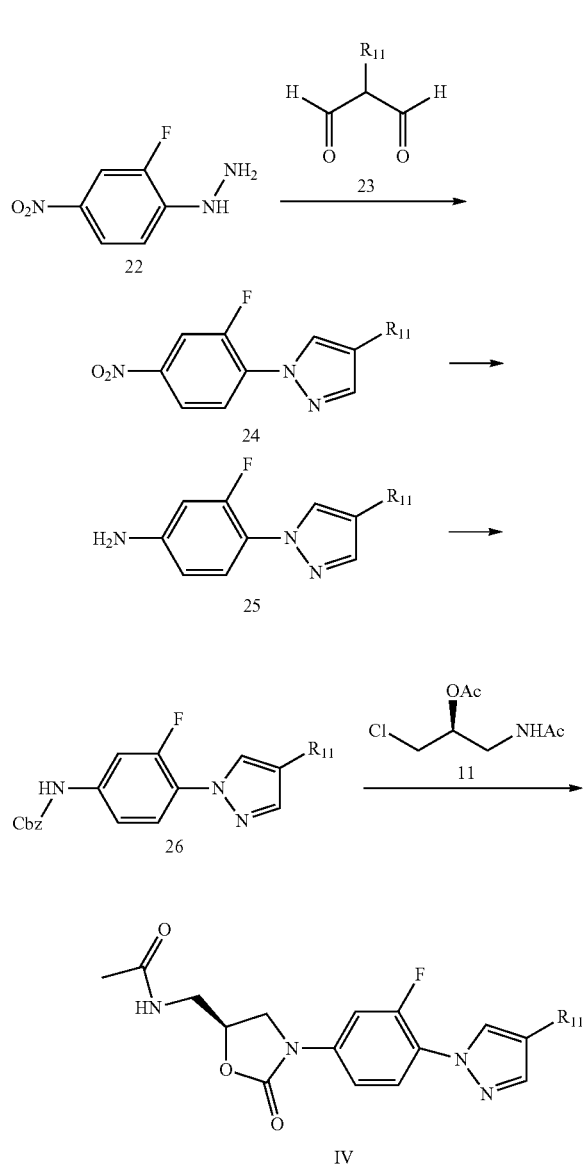

The preparation method 3 comprises the following steps:

(1) reacting Compound 22 with Compound 23 to obtain Compound 24;
(2) reducing Compound 24 to obtain Compound 25;
(3) reacting Compound 25 with Cbz-Cl to obtain Compound 26; and
(4) Compound 26 undergoing cyclization reaction with Compound 11 in the presence of t-BuOLi to obtain the product represented by Formula IV.

According to the method described above, the catalyst useful in Step (1) is selected from common inorganic and organic acids, preferably p-toluene sulfonic acid and hydrochloric acid. The reducing agent useful in Step (2) is Fe powder plus hydrochloric acid. The catalyst useful in Step (3) is a carbonate, preferably $K_2CO_3$.

In the aforesaid methods, $R_9$, $R_{10}$ and $R_{11}$ are each independently H, substituted phenyl,

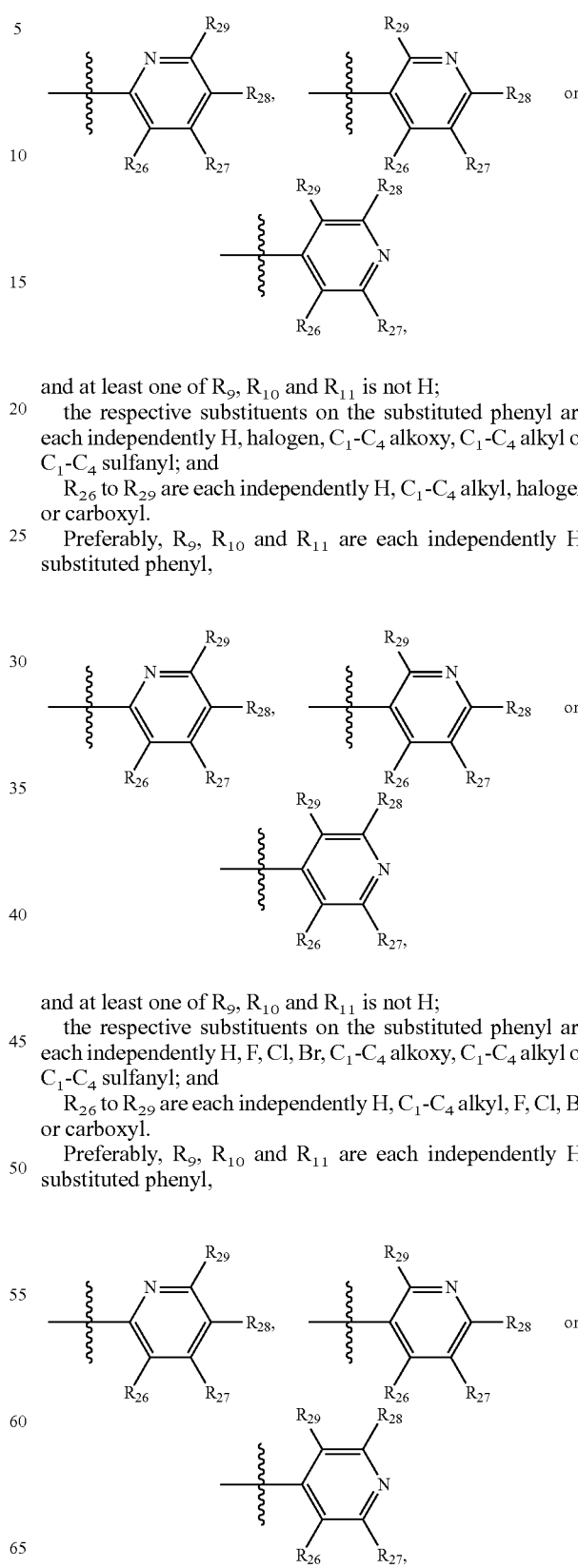

and at least one of $R_9$, $R_{10}$ and $R_{11}$ is not H;
the respective substituents on the substituted phenyl are each independently H, halogen, $C_1$-$C_4$ alkoxy, $C_1$-$C_4$ alkyl or $C_1$-$C_4$ sulfanyl; and
$R_{26}$ to $R_{29}$ are each independently H, $C_1$-$C_4$ alkyl, halogen or carboxyl.

Preferably, $R_9$, $R_{10}$ and $R_{11}$ are each independently H, substituted phenyl, and at least one of $R_9$, $R_{10}$ and $R_{11}$ is not H;
the respective substituents on the substituted phenyl are each independently H, F, Cl, Br, $C_1$-$C_4$ alkoxy, $C_1$-$C_4$ alkyl or $C_1$-$C_4$ sulfanyl; and
$R_{26}$ to $R_{29}$ are each independently H, $C_1$-$C_4$ alkyl, F, Cl, Br or carboxyl.

Preferably, $R_9$, $R_{10}$ and $R_{11}$ are each independently H, substituted phenyl, and at least one of $R_9$, $R_{10}$ and $R_11$ is not H;

the respective substituents on the substituted phenyl are each independently H, F, Cl, Br, $C_1$-$C_4$ alkoxy, $C_1$-$C_4$ alkyl or $C_1$-$C_4$ sulfanyl; and $R_{26}$ to $R_{29}$ are each independently H, F, Cl, Br or carboxyl.

Preferably, $R_9$, $R_{10}$ and $R_{11}$ are each independently H, substituted phenyl,

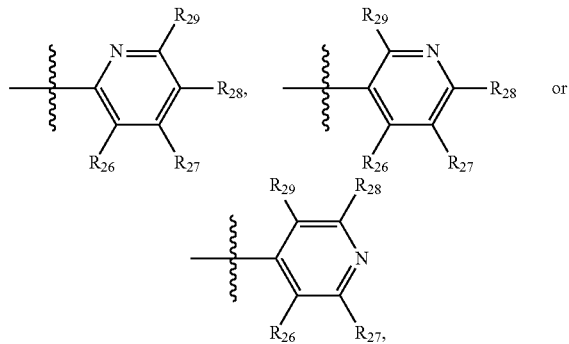

and at least one of $R_9$, $R_{10}$ and $R_{11}$ is not H;

the substituted phenyl is substituted by one or two substituents, each independently being H, Cl, Br, $C_1$-$C_4$ alkoxy, $C_1$-$C_4$ alkyl or $C_1$-$C_4$ sulfanyl; and $R_{26}$ to $R_{29}$ are each independently H, Cl, Br or carboxyl.

Preferably, $R_9$, $R_{10}$ and $R_{11}$ are each independently H,

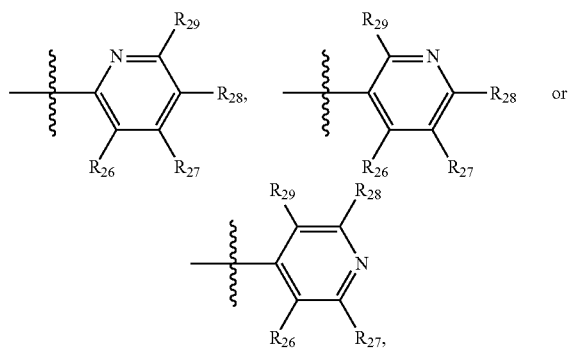

and at least one of $R_9$, $R_{10}$ and $R_{11}$ is not H; and $R_{26}$ to $R_{29}$ are each independently H, Cl, Br or carboxyl.

Most preferably, $R_9$, $R_{10}$ and $R_{11}$ are each independently H,

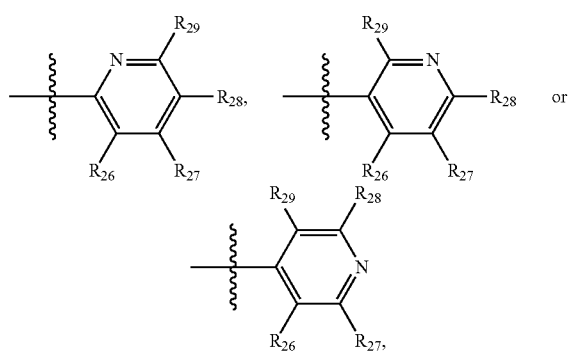

and at least one of $R_9$, $R_{10}$ and $R_{11}$ is not H; and $R_{26}$ to $R_{29}$ are each independently H, Br or carboxyl.

The compounds of the present invention include their isotopic compounds, racemates, optical active isomers, polycrystalline types, or mixtures thereof.

The invention also provides pharmaceutically acceptable salts of the oxazolidinone compounds. The term "salts" used herein refers to the pharmaceutically acceptable salts made from the oxazolidinone compounds of the present invention with hydrochloric acid, hydrobromic acid, hydrofluoric acid, sulfuric acid, phosphoric acid, nitric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, ethanesulfonic acid, isethionic acid, p-toluenesulfonic acid, benzenesulfonic acid, naphthalenesulfonic acid, trifluoroacetic acid or aspartic acid. The preferred salts are hydrochloride or mesylate of the said oxazolidinone compounds, optimally hydrochloride.

The invention also provides prodrugs of the oxazolidinone compounds. The term "prodrugs" used herein refers to the derivatives of the compounds of the present invention which per se may be of weak activity or even no activity, but, after being administered, can be converted into corresponding substances with bioactivity, for example, by metabolism, solvolysis or the like under physiological conditions.

The invention also provides pharmaceutically acceptable hydrates of the oxazolidinone compounds.

The invention also provides uses of the oxazolidinone compounds in preparation of antibiotic medicines.

In addition, the invention provides a pharmaceutical composition comprising the oxazolidinone compound and a pharmaceutically-acceptable auxiliary ingredient or ingredients, wherein the oxazolidinone compound has a structure represented by any of Formula I-V. The pharmaceutical composition may be in any form normally employed in the art, such as oral formulation, injection formulation, liniment, and so on.

Experimental results demonstrate that, as compared with Linezolid, the oxazolidinone compounds of the present invention display significant antibacterial activity (some even better than Linezolid) and substantially lower toxicity, and therefore, have better prospect for clinical application.

The beneficial effect of the present invention includes: the oxazolidinone compounds of the invention, which are new compounds obtained through a creative structural design and numerous screening, are sensitive to drug-resistant bacteria such as *staphylococcus aureus*, fecal coliform bacteria and *streptococcus pneumoniae* or have significant antibacterial activity for drug-resistant gram-positive bacteria, while exhibiting lower toxicity. Therefore, the oxazolidinone compounds of the invention provide new options for the development and clinical application of antibiotics.

DETAILED DESCRIPTION OF EMBODIMENTS OF THE INVENTION

Figure 1:
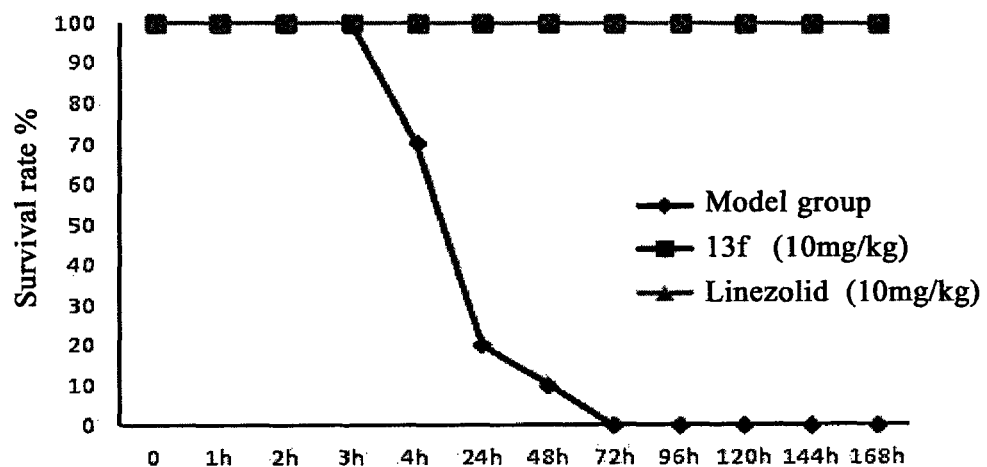
FIG. 1 shows the test result of the group with a dosage of 10 mg/kg.

Further description of the invention will be provided with reference to the embodiments as below. The embodiments are provided for the purpose of illustration only and shall not be construed to restrict the invention in any way.

TABLE 1

Structures of New Oxazolidinone Compounds

| Entry | Substituent | Chemical Name of Compound |
|---|---|---|
| 12a | pyridin-2-yl | (S)-N-((3-(3-fluoro-4-(3-(pyridin-2-yl)-1H-pyrazol-1-yl)phenyl)-2-oxooxazolidin-5-yl)methyl)acetamide |
| 13a | pyridin-3-yl | (S)-N-((3-(3-fluoro-4-(4-(pyridin-4-yl)-1H-pyrazol-1-yl)phenyl)-2-oxooxazolidin-5-yl)methyl)acetamide |
| 13b | p-tolyl | (S)-N-((3-(3-fluoro-4-(4-(p-tolyl)-1H-pyrazol-1-yl)phenyl)-2-oxooxazolidin-5-yl)methyl)acetamide |
| 13c | 4-methoxyphenyl | (S)-N-((3-(3-fluoro-4-(4-(4-methoxyphenyl)-1H-pyrazol-1-yl)phenyl)-2-oxooxazolidin-5-yl)methyl)acetamide |
| 13d | 4-chlorophenyl | (S)-N-((3-(3-fluoro-4-(4-(4-chlorophenyl)-1H-pyrazol-1-yl)phenyl)-2-oxooxazolidin-5-yl)methyl)acetamide |
| 13e | 5-carboxyl-pyridin-2-yl | (S)-N-((3-(3-fluoro-4-(4-(5-carboxyl-pyridin-2-yl)-1H-pyrazol-1-yl)phenyl)-2-oxooxazolidin-5-yl)methyl)acetamide |
| 13f | pyridin-2-yl | (S)-N-((3-(3-fluoro-4-(4-(pyridin-2-yl)-1H-pyrazol-1-yl)phenyl)-2-oxooxazolidin-5-yl)methyl)acetamide |
| 14a | pyridin-3-yl | (S)-N-((3-(3-fluoro-4-(5-(pyridin-3-yl)-1H-pyrazol-1-yl)phenyl)-2-oxooxazolidin-5-yl)methyl)acetamide |
| 14b | 6-bromopyridin-2-yl | (S)-N-((3-(3-fluoro-4-(5-(6-bromopyridin-2-yl)-1H-pyrazol-1-yl)phenyl)-2-oxooxazolidin-5-yl)methyl)acetamide |
| 14c | p-tolyl | (S)-N-((3-(3-fluoro-4-(5-(p-tolyl)-1H-pyrazol-1-yl)phenyl)-2-oxooxazolidin-5-yl)methyl)acetamide |

TABLE 1-continued

Structures of New Oxazolidinone Compounds

| Entry | Substituent | Chemical Name of Compound |
|---|---|---|
| 14d | 4-bromophenyl group | (S)-N-((3-(3-fluoro-4-(5-(4-bromophenyl)-1H-pyrazol-1-yl)phenyl)-2-oxooxazolidin-5-yl)methyl)acetamide |
| 14e | pyridin-2-yl group | (S)-N-((3-(3-fluoro-4-(5-(pyridin-2-yl)-1H-pyrazol-1-yl)phenyl)-2-oxooxazolidin-5-yl)methyl)acetamide |
| 14f | 4-(methylthio)phenyl group | (S)-N-((3-(3-fluoro-4-(5-(4-(methylthio)phenyl)-1H-pyrazol-1-yl)phenyl)-2-oxooxazolidin-5-yl)methyl)acetamide |
| 14g | 5-bromopyridin-2-yl group | (S)-N-((3-(3-fluoro-4-(5-(5-bromopyridin-2-yl)-1H-pyrazol-1-yl)phenyl)-2-oxooxazolidin-5-yl)methyl)acetamide |
| 14h | pyridin-4-yl group | (S)-N-((3-(3-fluoro-4-(5-(pyridin-4-yl)-1H-pyrazol-1-yl)phenyl)-2-oxooxazolidin-5-yl)methyl)acetamide |
| 14i | 4-fluorophenyl group | (S)-N-((3-(3-fluoro-4-(5-(4-fluorophenyl)-1H-pyrazol-1-yl)phenyl)-2-oxooxazolidin-5-yl)methyl)acetamide |
| 14j | 3,4-dimethoxyphenyl group | (S)-N-((3-(3-fluoro-4-(5-(3,4-dimethoxyphenyl)-1H-pyrazol-1-yl)phenyl)-2-oxooxazolidin-5-yl)methyl)acetamide |

EXAMPLE 1

Preparation of Intermediate
(S)—N-(2-acetyloxy-3-chloropropane) acetamide
(11)

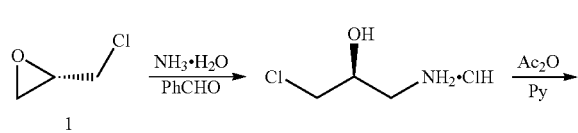

-continued

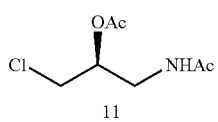

To 42.26 mL (540 mmol) (S)-epoxy chloropropane, 250 mL ethanol, 57 mL aqueous ammonia, and 56.5 mL benzaldehyde were added in sequence with stirring, upon which a white solid precipitated and then disappeared soon. The mixture was stirred for further 20 hours at room temperature, followed by rotary evaporation. Then, 81.7 mL concentrated hydrochloric acid was added to the residue, and the resultant mixture was stirred for 2 hours at room temperature, followed by rotary evaporation of the solvent. The solid obtained was recrystallized with ethanol. After chilling in a refrigerator overnight, filtration was performed to afford 53.6 g of (S)-1-amino-3-chloro-2-propanol hydrochloride as white powder. 53.6 g (281 mmol) of (S)-1-amino-3-chloro-2-propanol hydrochloride was dissolved in 165 mL (2050 mmol) of pyridine to form a solution. Then, 106 mL (1123 mmol) acetic anhydride ($Ac_2O$) was added dropwise into the solution at room temperature over 90 minutes, and the resultant mixture was stirred overnight. After rotary evaporation of the solvent, the pH of the residue was adjusted to be acidic with diluted hydrochloric acid, and then extracted three times with dichloromethane. The dichloromethane in the combined organic layer was removed by rotary evaporation to afford a crude product, which was recrystallized with a mixed solution of ethyl acetate and n-heptane (1:3) to obtain 50.2 g white crystal. The total yield of the two steps of reaction is 47.98%.

$^1$H-NMR (400 MHz, $CDCl_3$): δ 5.78 (br, s, 1H), 5.11-5.08 (m, 1H), 3.69 (dd, J=12 Hz, J=4.4 Hz, 1H), 3.67-3.57 (m, 2H), 3.55-3.48 (m, 1H).

ESI-MS m/z (M+H+): 194.14.

EXAMPLE 2

Preparation of N-benzyl-2-fluoro-4-nitroaniline (3)

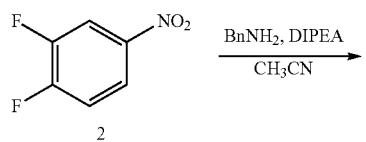

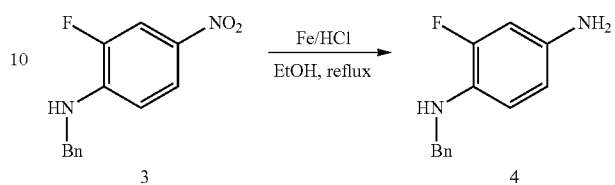

50 g (34.5 mL, 14.3 mmol) 3,4-difluoronitrobenzene and 44.6 mL (408.6 mmol) benzylamine were combined with 600 mL acetonitrile, and then 82.3 mL (471.5 mmol) N,N-diisopropylethylamine (DIPEA) was added thereto. The resultant mixture was slowly heated to reflux. The reaction substantially completed after refluxing 5 hours, as monitored by a real-time thin layer chromatography (TLC). Then, heating was stopped and the mixture was allowed to cool to room temperature, resulting in the precipitation of a colorless transparent crystal. The mixture was filtered when substantially no more crystal precipitated. The filtrate was evaporated in a rotatory evaporator to afford a yellowish solid, which was recrystallized with ethanol to obtain a yellow crystal. Then, the yellow crystal was dried and weighed 72.5 g, with a yield of 93.7%.

$^1$H-NMR (400 MHz, $CDCl_3$): δ 7.93 (m, 2H), 7.36 (m, 5H), 6.63 (t, J=8.4 Hz, 1H), 4.41 (s, 2H), 4.07 (broad s, 3H).

EXAMPLE 3

Preparation of N-(2-fluoro-4-aminophenyl)-N-benzylamine (4)

To 60 g (243.7 mmol) of the intermediate N-benzyl-2-fluoro-4-nitroaniline (3), 600 mL ethanol was added as a solvent. The resultant mixture was slowly heated to reflux and then 60 mL concentrated hydrochloric acid was added. After the reactant was completely dissolved, 55 g (974.6 mmol) of Fe powder was added in batches within 1 hour. Then, reflux was continued for five hours until the reaction almost completed. The mixture was cooled to room temperature and buffered to pH 8-9 with a saturated $Na_2CO_3$. Then, the mixture was filtrated, and the filtrate was evaporated to remove ethanol by rotatory evaporation. The residual water layer was extracted with ethyl acetate, and then the ethyl acetate layer was reversely extracted with 10% diluted hydrochloric acid solution. The ethyl acetate layer was discarded. The acid-water layer was adjusted to be basic with a NaOH solution and then extracted with ethyl acetate. Thus obtained ethyl acetate layer was rotary evaporated and 47 g of dark tan oily substance was obtained with a yield of 89.2%.

EXAMPLE 4

Preparation of Intermediate benzyl benzyl(4-(((benzyloxy)carbonyl)amino)-2-fluorophenyl)carbamate (5)

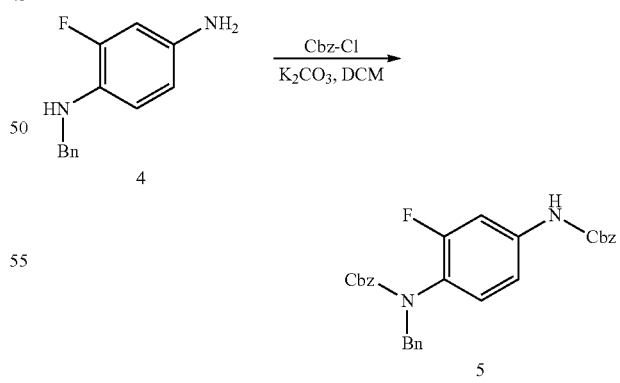

7 g (217.3 mmol) of N-(2-fluoro-4-aminophenyl)-N-benzyl amine (4) obtained from the aforesaid process was dissolved in 500 mL dichloromethane, then 60 g (434.6 mmol) of $K_2CO_3$ was added thereto, with stirring in an ice bath for 10 minutes. 92 mL (652 mmol) Cbz-Cl was dropped slowly to the mixture over 1 hour and then the mixture was warmed to room temperature. After completion of the reaction, 200 mL water was added to the reaction solution under stirring for 1 hour. The resultant mixture was allowed to stand for separation, and the dichloromethane layer was washed in sequence with 10% diluted hydrochloric acid and NaHCO$_3$ solution. The obtained dichloromethane layer was rotary evaporated to afford a light yellow oil, which was purified with column chromatography to obtain 80 g of a white solid, with a yield of 76.2%.

$^1$H-NMR (400 MHz, CDCl$_3$): δ 6.73-7.36 (m, 19H), 5.16 (m, 4H), 4.74 (d, J=2.4 Hz, 1H).

EXAMPLE 5

Preparation of Intermediate (6)

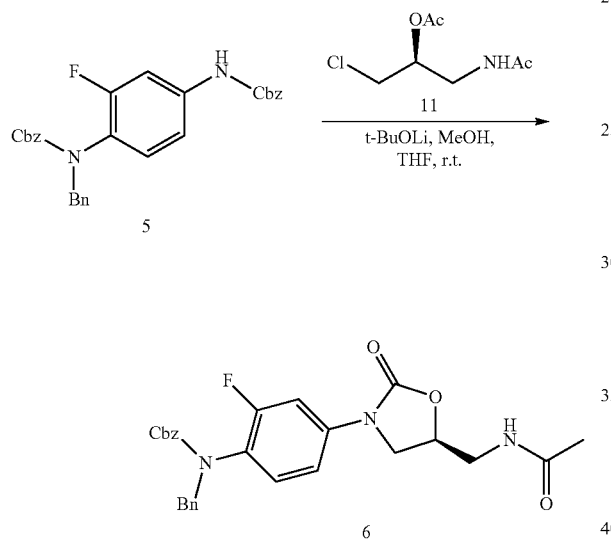

80 g (165.1 mmol) of compound (5) and 39.7 g (495.3 mmol) of t-BuOLi were put in a reaction vessel, then 300 mL redistilled tetrahydrofuran (THF) was added thereto. The air in the vessel was purged with nitrogen, and stirring was performed in an ice bath for 15 minutes. Then, 13.4 mL (330.2 mmol) methanol was added to the vessel. After stirring for another 15 minutes, 80 mL solution of the compound (S)—N-(2-acetyloxy-3-chloropropane) acetamide (11) in tetrahydrofuran was added to the vessel. Then, the mixture was warmed naturally to room temperature and stirred overnight. After completion of the reaction, 19 mL (330.2 mmol) acetic acid was added to the reaction mixture under stirring for 5 minutes. Then, the resultant solution was directly blended with 400 mL water and 400 mL dichloromethane for separation. Thus obtained aqueous layer was then extracted with dichloromethane for three times. The combined dichloromethane layer was dried with anhydrous Na$_2$SO$_4$ and evaporated by a rotary evaporator. After purification by column chromatography, a colorless oily substance was obtained, which was grinded with petroleum ether to afford a white solid. After filtration in vacuum, 37.8 g of white solid was obtained with a yield of 51.1%.

$^1$H-NMR (400 MHz, CDCl$_3$): δ 7.47 (d, J=11.6 Hz 1H), 7.27 (m, 10H), 7.00 (dd, J=8 Hz, J=24.4 Hz, 2H), 6.17 (s, H), 5.19 (d, J=7.6 Hz, 2H), 4.81-4.71 (m, 3H), 3.98 (t, J=8.8 Hz, 1H), 3.73-3.55 (m, 3H), 2.00 (s, 1H).

EXAMPLE 6

Preparation of Intermediate (S)—N-[3-[(3-fluoro-4-aminophenyl)-2-oxo-oxazolidin-5-yl]methyl]acetamide (7)

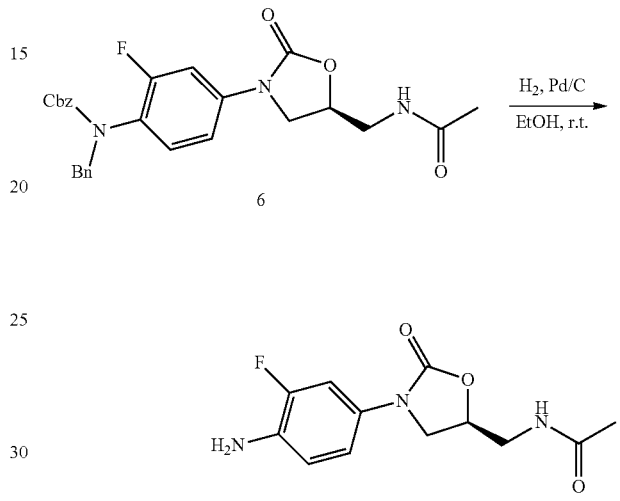

37 g of compound (6) was dissolved in 350 ml of ethanol and then 7 g of Pd/C was added into the resulting solution. The reaction system was stirred overnight under room temperature with a flow of hydrogen. After completion of the reaction, Pd/C was removed by vacuum filtration. The filtrate was rotary evaporated to remove the solvent, and then was recrystallized with ethyl alcohol to afford 19 g offwhite solid with a yield of 94.5%.

$^1$H-NMR (400 MHz, CDCl$_3$): δ 8.25 (t, J=5.6 Hz, 1H), 7.31 (dd, J=2 Hz, J=13.2 Hz, 1H), 6.91 (dd, J=1.6 Hz, J=8.4 Hz, 1H), 6.76 (t, J=10 Hz, 1H), 5.04 (s, 2H), 4.66 (m, 1H), 4.01 (t, J=8.8 Hz, 1H), 3.64 (dd, J=6.4 Hz, J=12.8 Hz, 1H), 3.40-3.36 (m, 2H), 1.83 (s, 1H).

EXAMPLE 7

Preparation of Intermediate (S)—N-((3-(3-fluoro-4-hydrazinophenyl)-2-oxooxazolidin-5-yl)methyl)acetamide (8)

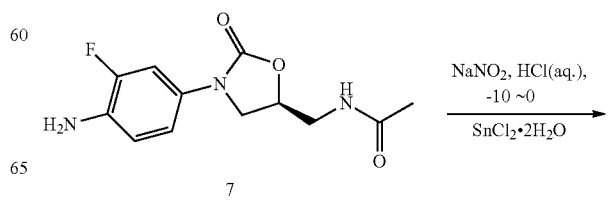

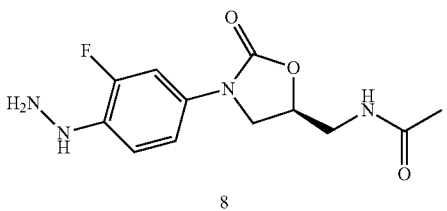

3 g (11.22 mmol) of (S)—N-((3-(4-amino-3-fluorophenyl)-2-oxooxazolidin-5-yl) methyl)acetamide (7) was dissolved in a blend of 6 mL methanol, 12 mL water and 3 mL concentrated hydrochloric acid. The resultant mixture was stirred for 10 minutes in an ice-salt bath to maintain the internal temperature below −5° C. Then, a NaNO$_2$ solution prepared in advance was slowly dropped into the mixture. After completion of the addition, the mixture was stirred in the ice-salt bath for another 30 minutes to prepare a reaction solution of diazonium salt. Meanwhile, 6.08 g of SnCl$_2$ was dissolved in a concentrated hydrochloric acid under vigorous stirring in an ice-salt bath. The reaction solution of diazonium salt prepared above was slowly dropped into the SnCl$_2$ solution in hydrochloric acid, and then the mixture was warmed naturally to room temperature and stirred for another 2 hours. After completion of the reaction, the reactant was buffered to a pH between 7 and 8 with 1 ON NaOH solution. After the solvent was evaporated in a rotary evaporator, the resultant material was repeatedly grinded with methanol. After the solvent methanol was rotary evaporated, the residue was recrystallized with ethanol and then filtered to afford a light yellow crystalline solid weighed 2.2 g, with a yield of 70%. The product was kept under low temperature and in a dry place.

$^1$H-NMR (400 MHz, CDCl$_3$): δ 8.25 (t, J=6 Hz, 1H), 7.35 (dd, J=2.4 Hz, J=14 Hz, 1H), 7.14 (t, J=8.8 Hz, 1H), 7.07 (dd, J=2 Hz, J=9.2 Hz, 1H), 6.57 (s, 1H), 4.67 (m, 1H), 4.01 (m, 3H), 3.67 (dd, J=6.8 Hz, J=9.2 Hz, 1H), 3.39 (t, J=5.2 Hz 2H), 1.83 (s, 1H).

EXAMPLE 8

Preparation of Intermediate (E)-3-(dimethylamino)-1-(pyridin-3-yl)prop-2-en-1-one (10a)

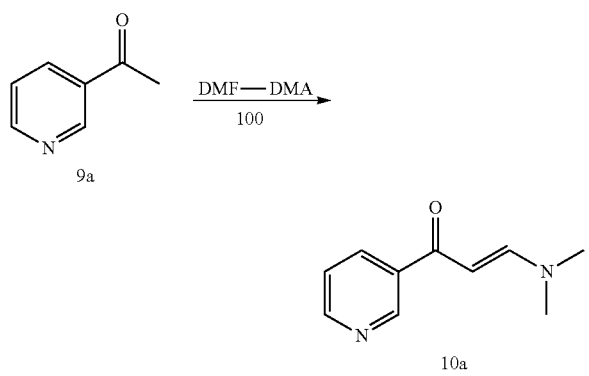

To 0.907 mL (8.25 mmol) 3-acetopyridine, 2.2 mL (16.5 mmol) N,N-DMF-DMA was added, and the resultant mixture was slowly heated to reflux for 6 hours. After completion of the reaction as monitored with TLC, heating was stopped and the resultant mixture was cooled to room temperature. Then, 4 mL of a blend solvent of petroleum ether and ethyl acetate (3:1) was added to the mixture to precipitate a solid. The solid was filtered and washed with a petroleum ether-ethyl acetate mixture (3:1). After drying, 1.15 g of a yellow solid was obtained, with a yield of 79.4%.

$^1$H-NMR (400 MHz, CDCl$_3$): δ 9.08 (s, 1H), 8.67 (m, 1H), 8.21 (m, 1H), 7.85 (d, J=12.4 Hz, 1H), 7.37 (m, 1H).

EXAMPLE 9

Preparation of Intermediates 10b-j (1) Intermediate 10b was prepared by the same steps as those of 10a, with a yield of 72.8%.

$^1$H-NMR (400 MHz, CDCl$_3$): δ 8.10 (d, J=7.2 Hz, 1H), 7.91 (d, J=12.8 Hz, 1H), 7.65 (t, J=8 Hz, 1H), 7.54 (d, J=8 Hz, 1H), 6.40 (d, J=12 Hz, 1H), 3.19 (s, 3H), 3.02 (s, 3H).

(2) Intermediate 10c was prepared by the same steps as those of 10a, with a yield of 82.6%.

$^1$H-NMR (400 MHz, CDCl$_3$): δ 7.80 (m, 3H), 7.21 (t, J=8 Hz, 2H), 5.72 (d, J=12.4 Hz, 1H), 3.12 (s, 3H), 2.94 (s, 3H), 2.393 (s, 3H).

(3) Intermediate 10d was prepared by the same steps as those of 10a, with a yield of 73.1%.

$^1$H-NMR (400 MHz, CDCl$_3$): δ 7.82 (d, J=12.4 Hz, 1H), 7.77 (t, J=14.8 Hz, 2H), 7.54 (t, J=2 Hz, 2H), 5.66 (d, J=12.4 Hz, 1H), 3.16 (s, 3H), 2.94 (d, J=8.4 Hz, 3H).

(4) Intermediate 10e was prepared by the same steps as those of 10a, with a yield of 70.3%.

$^1$H-NMR (400 MHz, CDCl$_3$): δ 8.62 (d, J=0.4 Hz, 1H), 8.15 (d, J=8 Hz, 1H), 7.92 (d, J=12.8 Hz, 1H), 7.80 (m, 1H), 7.36 (m, 1H), 6.45 (d, J=12.4 Hz, 1H), 3.18 (s, 3H), 3.00 (s, 3H).

(5) Intermediate 10f was prepared by the same steps as those of 10a, with a yield of 82.2%.

$^1$H-NMR (400 MHz, CDCl$_3$): δ 7.83 (m, 4H), 7.26 (m, 1H), 5.70 (d, J=12 Hz, 1H), 3.11 (m, 6H), 2.54 (m, 3H).

(6) Intermediate 10g was prepared by the same steps as those of 10a, with a yield of 80.1%.

$^1$H-NMR (400 MHz, CDCl$_3$): δ 8.81 (d, J=2.4 Hz, 1H), 8.05 (m, 1H), 7.85 (d, J=12.4 Hz, 1H), 7.55 (s, 1H), 5.61 (d, J=12 Hz, 1H), 3.20 (s, 3H), 2.96 (s, 3H)

(7) Intermediate 10h was prepared by the same steps as those of 10a, with yield of 75.4%.

$^1$H-NMR (400 MHz, CDCl$_3$): δ 8.70 (d, J=5.2 Hz, 2H), 7.85 (d, J=14 Hz, 1H), 7.68 (d, J=5.6 Hz, 2H), 5.65 (d, J=12.4 Hz, 1H), 3.19 (s, 3H), 3.00 (s, 3H).

(8) Intermediate 10i was prepared by the same steps as those of 10a, with a yield of 85.7%.

(9) Intermediate 10j was prepared by the same steps as those of 10a, with a yield of 83.8%.

$^1$H-NMR (400 MHz, CDCl$_3$): δ 7.81 (d, J=12.4 Hz, 1H), 7.56 (d, J=1.6 Hz, 1H), 7.51 (m, 1H), 6.87 (d, J=8.4 Hz, 1H), 5.72 (d, J=12.4 Hz, 1H), 3.94 (d, J=9.2 Hz, 6H), 2.84 (m, 6H)

EXAMPLE 10

Preparation of 2-fluoro-4-nitrophenylhydrazine (22)

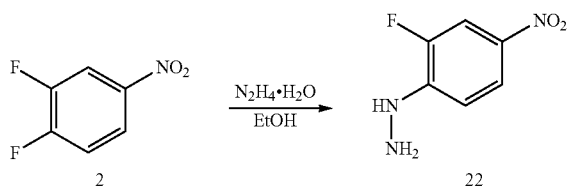 [SMILES: "EtOH" ; O=[N+]([O-])c1ccc(F)c(F)c1 ; "N2H4·H2O" ; NNc1ccc([N+](=O)[O-])cc1F]

690 μL 3,4-difluoronitrobenzene was added to 15 mL anhydrous ethanol, and then the blend was heated to reflux. Hydrazine hydrate (611.5 μL) was slowly dropped into the blend and the resultant mixture was refluxed for another 2 hours to complete reaction, after which the reaction mixture was cooled down to room temperature. The yellow solid precipitated upon cooling was filtered. The filter cake was washed with petroleum ether, and then was dried to get 884.5 mg of a yellow solid, with a yield of 92.2%.

$^1$H-NMR (400 MHz, CDCl$_3$): δ 8.05 (dd, J=6.4 Hz, J=2.4 Hz, 1H), 7.89 (dd, J=12 Hz, J=2.4 Hz, 1H), 7.23 (d, J=8.8 Hz, 1H), 6.01 (s, 1H), 3.75 (s, 2H).

EXAMPLE 11

Preparation of 2-[1-(2-fluoro-4-nitrophenyl)-1H-pyrazol-4-yl]pyridine (24f)

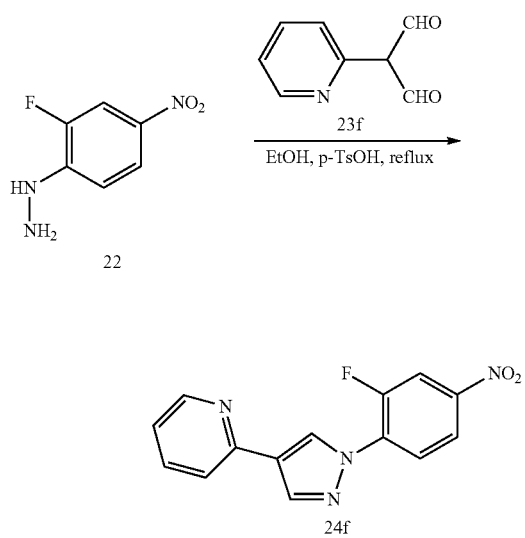

2-fluoro-4-nitrophenylhydrazine (700 mg) and 2-(2-pyridyl)malondialdehyde (610 mg) was dissolved in ethanol (30 mL). Then, p-toluenesulfonic acid (70 mg) was added into the mixture to serve as a catalyst. The reaction mixture was heated to reflux for 2 h. After completion of the reaction, the resultant mixture was cooled down to room temperature and filtered to obtain 993 mg brown solid, with a yield of 85.4%.

$^1$H-NMR (400 MHz, DMSO-d$_6$): δ 9.09 (s, 1H), 8.69 (d, J=5.2 Hz, 1H), 8.62 (s, 1H), 8.50 (dd, J=11.6 Hz, J=2.4 Hz), 8.30-8.21 (m, 2H), 7.50-7.46 (m, 2H), 7.11 (d, J=8.8 Hz, 1H).

EXAMPLE 12

Synthesis of 2-[1-(2-fluoro-4-aminophenyl)-1H-pyrazol-4-yl]pyridine (25f)

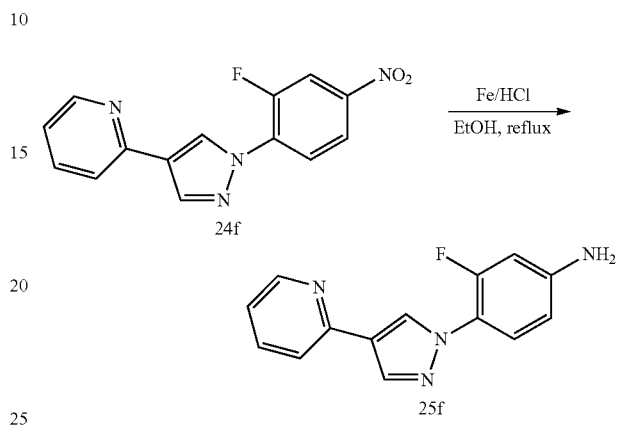

900 mg of 2-(1-(2-fluoro-4-nitrophenyl)-1H-pyrazol-4-yl)pyridine (24f) was dissolved in 25 mL ethyl alcohol (95%), and then the mixture was heated to reflux. HCl (4N, 660 μL) was added to the mixture, and then Fe powder (886.5 mg) was added in batches over 15 minutes, under stirring and refluxing. TLC monitoring was performed to determine completion of the reaction, after which the mixture was cooled down to room temperature and buffered to pH 9-10 with a saturated Na$_2$CO$_3$ solution. Then, the iron sludge in the mixture was removed by vacuum filtration. The filtrate was rotary evaporated, dissolved with water (20 mL), and then extracted with ethyl acetate for three times. The combined organic phase was washed with diluted hydrochloric acid (5%) until the organic phase was free of fluorescence. Then, the combined water phase was buffered to be basic (pH>7) with a saturated sodium bicarbonate solution. The resultant solution was extracted with ethyl acetate for three times. The combined organic phase was dried and rotary evaporated to obtain 540 mg of a light brown solid, with a yield of 67.2%. Thus obtained crude product can be directly used for the next step without further purification.

$^1$H-NMR (400 MHz, DMSO-d$_6$): δ 9.89 (s, 2H), 9.48 (s, 1H), 8.88 (s, 1H), 8.73 (d, J=6 Hz, 1H), 8.58-8.54 (m, 1H), 8.46 (d, J=8.4 Hz, 1H), 7.84 (t, J=6.8 Hz, 1H), 7.66 (t, J=8.4 Hz, 1H), 7.04 (d, J=12.8 Hz, 1H), 6.95 (d, J=8.8 Hz, 1H).

EXAMPLE 13

Synthesis of N-benzyloxycarbonyl-3-fluoro-4-(4-(pyridin-2-yl)-1H-pyrazol-1-yl)aniline (26f)

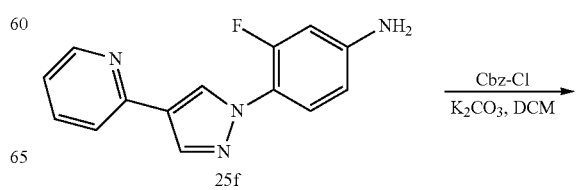

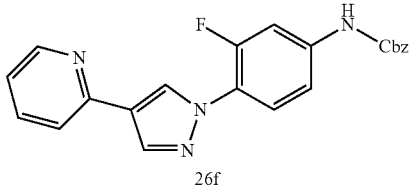

26f 200 mg of 2-(1-(2-fluoro-4-aminophenyl)-1H-pyrazol-4-yl)pyridine (25f) was dissolved in 5 mL dichloromethane, with addition of 194.3 mg $K_2CO_3$. Then, 990 μL Cbz-Cl was slowly dropped into the resultant mixture maintained in an ice bath. After completion of the addition, the ice bath was removed. The reaction mixture was warmed naturally to room temperature and reacted for 2 hours. TLC monitoring was performed to determine the completion of the reaction, after which water was added into the reaction solution. The mixture was extracted with dichloromethane for three times. The combined organic phase was dried and rotary evaporated. The residue obtained was repeatedly washed with petroleum ether until the excess Cbz-Cl was completely removed, thereby affording 260 mg of a light yellow solid, with a yield of 95.1%.

$^1$H-NMR (400 MHz, $CDCl_3$): δ 8.60 (d, J=4.8 Hz, 1H), 8.48 (d, J=2 Hz, 1H), 8.21 (s, 1H), 7.82 (t, J=8.8 Hz, 1H), 7.72-7.68 (m, 1H), 7.64 (d, J=12.8 Hz, 1H), 7.54 (d, J=8 Hz, 1H), 7.43-7.36 (m, 4H), 7.17-7.14 (m, 1H), 7.09 (dd, J=8.8 Hz, J=1.2 Hz, 1H), 6.86 (s, 1H), 5.23 (s, 1H).

EXAMPLE 14

Synthesis of (Z)-3-(dimethylamino)-1-(pyridin-2-yl)prop-2-en-1-one (16a)

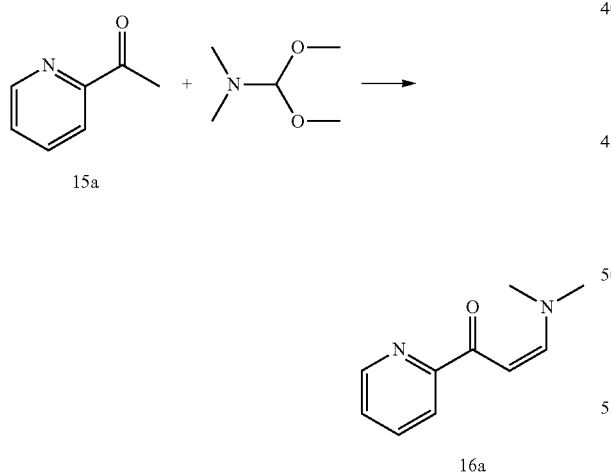

2-acetopyridine (15a) (5 g, 4.6 mL, 41 mmol) was mixed with N,N-DMF-DMA (8.8 g, 9.8 mL, 73.8 mmol), and reacted at 90° C. for 6 hours. Then, the reaction mixture was cooled to room temperature, resulting in a substantial amount of yellow precipitate. The yellow precipitate was suction-filtered, and the filter cake was recrystallized with ethyl acetate to afford the product 16a, a yellow crystal in bulk form (6.1 g), with a yield of 92.3%.

$^1$H-NMR (400 MHz, $CDCl_3$): δ 8.63 (d, J=4 Hz, 2H), 8.15 (d, J=8 Hz, 1H), 7.92 (d, J=12.8 Hz, 1H), 7.80 (m, 1H), 7.36 (m, 1H), 6.45 (d, J=12.4 Hz, 1H), 3.18 (s, 3H), 3.00 (s, 3H).

EXAMPLE 15

Synthesis of 2-(3-pyrazolyl)pyridine (17a)

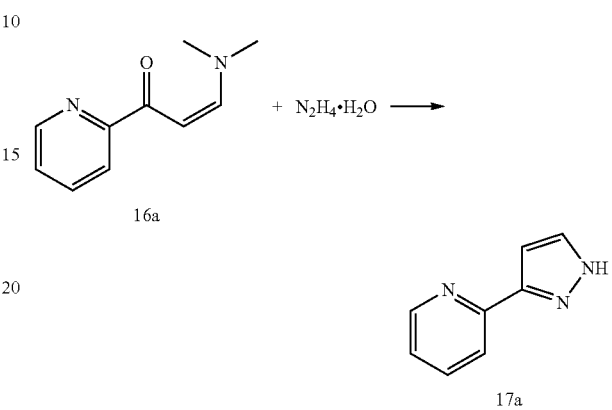

Compound 16a (1 g, 6.2 mmol) obtained from the aforesaid process and hydrazine hydrate (2 mL) were dissolved in ethanol (3.3 mL), and reacted at 60° C. for 0.5 hour. Then, the mixture was cooled to room temperature, and then the solvent was removed in vacuum to afford the product 17a (874.7 mg) as a faint yellow solid, with a yield of 97.3%.

$^1$H-NMR (400 MHz, $CDCl_3$): δ 8.66 (d, J=4.8 Hz, 1H), 7.75 (d, J=3.6 Hz, 2H), 7.67 (d, J=2 Hz, 1H), 7.23-7.27 (m, 1H), 6.81 (d, J=2 Hz, 1H).

EXAMPLE 16

Synthesis of 2-(1-(2-fluoro-4-nitrophenyl)-3-pyrazolyl)pyridine (18a)

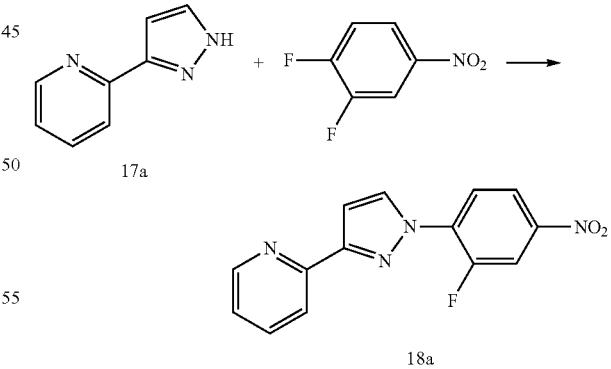

Compound 17a (1 g, 6.9 mmol) obtained from the aforesaid process and 3,4-difluoro-nitrobenzene (0.74 mL) were dissolved in N,N-dimethylformamide (20 mL), and then anhydrous potassium carbonate (1.9 g) was added thereto. The mixture was reacted at 100° C. for 4 hours. After completion of the reaction, the reactant mixture was cooled to room temperature. Water was added to the mixture, resulting in a substantial amount of precipitate. Then, the precipitate was suction-filtered, and the filter cake was recrystallized with acetone to get the product 18a as a white powder (1.7 g), with a yield of 93.4%.

$^1$H-NMR (400 MHz, CDCl$_3$): δ 8.69-8.70 (m, 1H), 8.39-8.44 (m, 1H), 8.26-8.27 (m, 1H), 8.15-8.21 (m, 2H), 8.11-8.13 (m, 1H), 7.78-7.82 (m, 1H), 7.30-7.32 (m, 1H), 7.22 (d, J=2.4 Hz, 1H)

EXAMPLE 17

Synthesis of 3-fluoro-4-(3-(pyridin-2-yl)-1H-pyrazol-1-yl)aniline (19a)

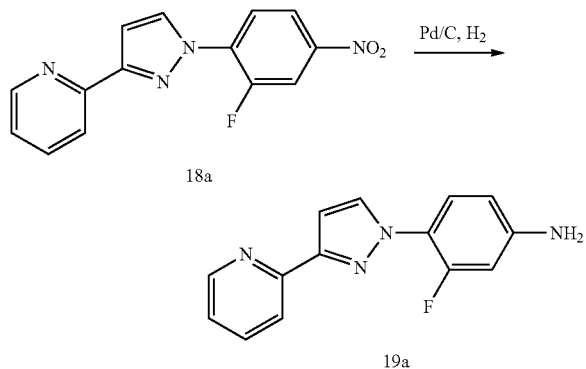

The above-described product 18a (7.87 g, 27.7 mmol) was dissolved in ethanol (50 mL), together with Pd/C (0.787 g). The mixture was reacted overnight at room temperature with a flow of hydrogen. After completion of the reaction, the solvent was evaporated. After recrystallization with ethyl acetate/petroleum ether, the product 19a (5.9 g) was obtained as a yellow solid, with a yield of 83.4%.

$^1$H-NMR (400 MHz, CDCl$_3$): δ 8.62 (d, J=4 Hz, 1H), 8.07 (d, J=8 Hz, 1H), 7.87 (t, J=2.4 Hz, 1H), 7.73 (m, 1H), 7.65 (t, J=8.8 Hz, 1H), 7.22 (m, 1H), 7.08 (d, J=2.4 Hz, 1H), 6.55-6.50 (m, 2H), 3.89 (s, 2H).

EXAMPLE 18

Synthesis of 3-fluoro-4-(3-(2-pyridyl)-1-pyrazolyl) phenyl carbamic acid benzyl ester (20a)

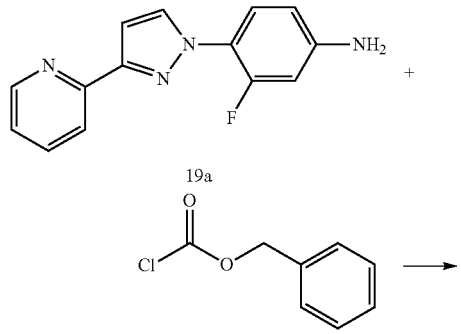

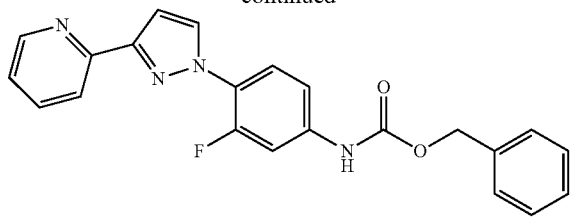

The above-described product 19a (1 g, 3.9 mmol) was dissolved in dichloromethane (4 mL), and then anhydrous potassium carbonate (0.6 g) was added thereto. Then, Cbz-Cl (1.863 g, 1.537 mL) was slowly dropped, at a rate of 1-2 drops per second, into the mixture maintained in an ice-salt bath. The resultant mixture was reacted for 4 hours at room temperature. After completion of the reaction, water was added into the reaction mixture, followed by extraction with ethyl acetate. The combined ethyl acetate phase was evaporated in vacuum to get a crude product, which was recrystallized with acetone to afford the product 20a (1.235 g) as a white solid, with a yield of 80.8%.

$^1$H-NMR (400 MHz, CDCl$_3$): δ 8.66 (dd, J=0.8 Hz, J=4 Hz, 1H), 8.08 (d, J=7.6 Hz, 1H), 8.00 (t, J=2.8 Hz, 1H), 7.90 (t, J=8.8 Hz, 1H), 7.76 (m, 1H), 7.61 (d, J=13.2 Hz, 1H), 7.42-7.34 (m, 5H), 7.26-7.23 (m, 1H), 7.14 (d, J=2.4 Hz, 1H), 7.09 (dd, J=1.6 Hz, J=8.8 Hz, 1H), 6.93 (s, 1H), 5.22 (s, 2H).

EXAMPLE 19

Synthesis of Target Compound (S)—N-((3-(3-fluoro-4-(3-(pyridin-2-yl)-1H-pyrazol-1-yl)phenyl)-2-oxooxazolidin-5-yl)methyl)acetamide (12a)

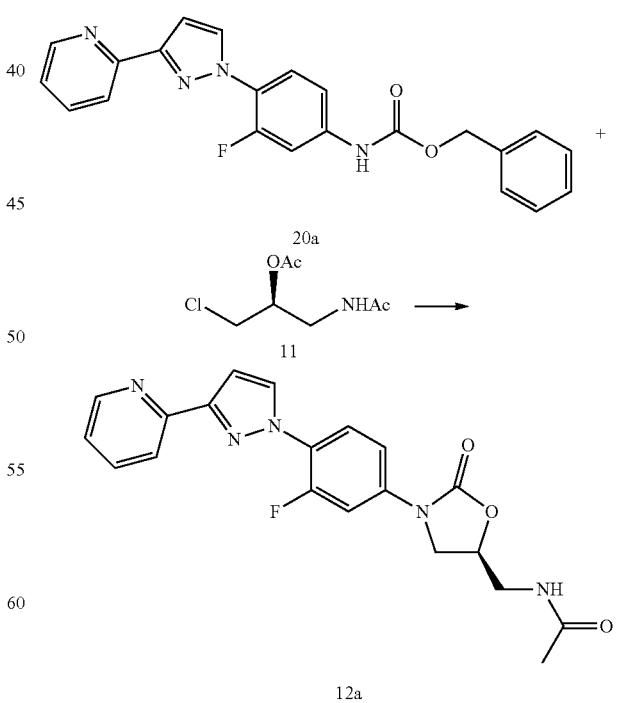

The above-described product 20a (1.235 g, 3.18 mmol) and lithium tert-butoxide (0.762 g) were mixed in a reaction vessel. After the air in the vessel was purged with nitrogen, tetrahydrofuran (5 mL) was added into the vessel and the mixture was cooled in an ice-water bath for 5 minutes. Then, methanol (0.204 g, 0.258 mL) was added. Two minutes later, a solution of Compound (11) (1.237 g) in tetrahydrofuran (5 mL) was added. Then, the water-ice bath was removed and the resultant mixture was reacted for 14 hours at room temperature. After completion of the reaction, ethyl acetate was added to the reactant mixture, resulting in a substantial amount of precipitate. Thus obtained mixture was suction-filtered, and the filter cake was recrystallized with a solvent mixture of ethyl acetate/petroleum ether to afford the product 12a (575 mg) as a white powder, with a yield of 45.7%.

$^1$H-NMR (400 MHz, CDCl$_3$): δ 8.64 (d, J=4.8 Hz, 1H), 8.29 (d, J=5.6 Hz, 2H), 8.04 (d, J=8 Hz, 1H), 7.86-7.94 (m, 2H), 7.75-7.79 (m, 1H), 7.50-7.52 (m, 1H), 7.37-7.39 (m, 1H), 7.11 (d. J=2.4 Hz, 1H), 4.77-4.80 (m, 1H), 4.20 (t, J=8.8 Hz, 1H), 3.79-3.83 (m, 1H), 3.44-3.47 (m, 2H), 1.85 (s, 3H).

$^{13}$C-NMR (DMSO-d$_6$): δ 170.04, 154.62, 153.98, 152.52, 152.17, 151.00, 149.38, 138.58, 136.94, 133.07, 125.20, 123.07, 119.75, 114.03, 106.24, 106.03, 71.81, 47.24, 41.37, 22.41.

ESI-MS m/z 396.1 (M+H+).

EXAMPLE 20

Synthesis of Target Compound (S)—N-((3-(3-fluoro-4-(4-(pyridin-4-yl)-1H-pyrazol-1-yl)phenyl)-2-oxooxazolidin-5-yl)methyl)acetamide (13a)

100 mg (0.354 mmol) of (S)—N-{[3-(3-fluoro-4-hydrazinophenyl)-2-oxooxazolidin-5-yl]methyl}-acetamide and 52.8 mg (0.354 mmol) of 2-(4-pyridyl)malondialdehyde were combined with 5 mL ethanol as a solvent. Then, the resultant mixture was slowly heated to reflux, thereby the solid was substantially dissolved. TLC monitoring was performed to determine completion of the reaction. Then, the resultant mixture was cooled to room temperature and vacuum filtered to afford the product (13a) as a light yellow solid, with a yield of 66.3%, melting point: 203.8-205.0° C., HPLC: 99.97%.

$^1$H-NMR (DMSO-d$_6$): δ 8.89 (s, 1H), 8.56 (d, J=5.2 Hz, 2H), 8.449 (s, 1H), 8.30 (t, J=5.6 Hz, 1H), 7.85 (t, J=8.8 Hz, 1H), 7.78 (d, J=14 Hz, 1H), 7.73 (d, J=5.2 Hz, 2H), 7.51 (d, J=8.8 Hz, 1H), 4.78 (m, 1H), 4.19 (t, J=8.8 Hz, 1H), 3.81 (t, J=7.2 Hz, 1H), 3.45 (t, J=5.2 Hz, 2H), 1.85 (s, 3H).

$^{13}$C-NMR (DMSO-d$_6$): δ 170.01, 154.61, 153.98, 152.15, 150.12, 139.05, 138.92, 138.81, 129.73, 125.37, 122.70, 121.28, 119.83, 114.00, 106.16, 105.90, 71.82, 47.20, 41.34, 22.42.

MS (ITMS) m/z 418.1 (M+Na$^+$).

EXAMPLE 21

Synthesis of Target Compounds 13b-f (1) Synthesis of Target Compound (S)—N-((3-(3-fluoro-4-(4-(p-tolyl)-1H-pyrazol-1-yl) phenyl)-2-oxooxazolidin-5-yl)methyl)acetamide (13b)

Compound 13b was prepared by the same steps as those of 13a, in the form of a light yellow solid, yield: 69.5%, melting point: 221.5-222.8° C., HPLC: 99.8%.

$^1$H-NMR (DMSO-d$_6$): δ 8.59 (s, 1H), 8.30 (t, J=5.6 Hz, 1H), 8.23 (s, 1H), 7.84 (t, J=9.2 Hz, 1H), 7.77 (d, J=13.6 Hz, 1H), 7.61 (d, J=8.0 Hz, 2H), 7.49 (d, J=8.8 Hz, 1H), 7.22 (d, J=8 Hz, 2H), 4.78 (m, 1H), 4.19 (t, J=9.2 Hz, 1H), 3.80 (t, J=7.2 Hz, 1H), 3.45 (t, J=4.8 Hz, 2H), 2.32 (s, 3H), 1.85 (s, 3H).

$^{13}$C-NMR (DMSO-d$_6$): δ 170.00, 154.42, 153.99, 151.96, 138.41, 135.77, 129.41, 128.70, 127.54, 125.26, 125.06, 123.76, 120.56, 120.08, 114.00, 106.21, 105.96, 71.79, 47.19, 41.34, 22.42, 20.71.

ESI-MS m/z 431.1 (M+N$^+$).

(2) Synthesis of Target Compound (S)—N-((3-(3-fluoro-4-(4-(4-methoxyphenyl)-1H-pyrazol-1-yl) phenyl)-2-oxooxazolidin-5-yl)methyl)acetamide (13c)

Compound 13c was prepared by the same steps as those of 13a, in the form of a light yellow solid, yield: 80.7%, melting point: 226.1-227.8° C., HPLC: 98.7%.

$^1$H-NMR (DMSO-d$_6$): δ 8.53 (d, J=1.6 Hz, 1H), 8.30 (t, J=5.6 Hz, 1H), 8.19 (s, 1H), 7.85 (t, J=8.8 Hz, 1H), 7.76 (dd, J=14 Hz, J=2 Hz, 1H), 7.64 (d, J=8.8 Hz, 2H), 7.49 (d, J=8.8 Hz, 1H), 6.97 (d, J=8.4 Hz, 2H), 4.78 (m, 1H), 4.19 (t, J=9.2 Hz, 1H), 3.80 (m, 4H), 3.45 (t, J=5.6 Hz, 2H), 1.85 (s, 3H).

$^{13}$C-NMR (DMSO-d$_6$): δ 170.00, 158.10, 154.37, 153.99, 151.92, 138.30, 127.09, 126.60, 125.00, 124.06, 123.61, 123.19, 123.09, 114.14, 114.01, 106.22, 105.96, 71.79, 55.06, 47.19, 41.34, 22.42.

ESI-MS m/z 447.1 (M+Na$^+$).

(3) Synthesis of Target Compound (S)—N-((3-(3-fluoro-4-(4-(4-chlorophenyl)-1H-pyrazol-1-yl)phenyl)-2-oxooxazolidin-5-yl)methyl)acetamide (13d)

Compound 13d was prepared by the same steps as those of 13a, in the form of a pale white solid, yield: 72.2%, melting point: 237.5-238.2° C., HPLC: 98.2%.

$^1$H-NMR (DMSO-d$_6$): δ 8.69 (s, 1H), 8.31 (s, 2H), 7.84 (t, J=8.8 Hz, 1H), 7.77 (m, 3H), 7.48 (m, 3H), 4.78 (m, 1H), 4.19 (t, J=9.2 Hz, 1H), 3.80 (t, J=6.8 Hz, 1H), 3.45 (t, J=5.2 Hz, 2H), 1.85 (s, 3H).

$^{13}$C-NMR (DMSO-d$_6$): δ 170.00, 154.48, 153.98, 152.02, 138.60, 138.52, 130.94, 130.58, 128.81, 128.27, 127.04, 125.16, 123.01, 122.75, 114.00, 106.20, 105.94, 71.80, 47.20, 41.35, 22.42.

ESI-MS m/z 451.1 (M+Na$^+$).

(4) Synthesis of Target Compound (S) N-((3-(3-fluoro-4-(4-(5-carboxyl-pyridin-2-yl)-1H-pyrazol-1-yl)phenyl)-2-oxooxazolidin-5-yl)methyl)acetamide (13e)

Compound 13e was prepared by the same steps as those of 13a, in the form of a white solid, yield: 78.1%, melting point: 279.6-280.2° C., HPLC: 98.5%.

$^1$H-NMR (DMSO-d$_6$): δ 13.34 (s, 1H), 9.05 (d, J=0.8 Hz, 1H), 8.88 (d, J=1.6 Hz, 1H), 8.46 (s, 1H), 8.29 (m, 2H), 7.96 (d, J=8.4 Hz, 1H), 7.88 (t, J=8.8 Hz, 1H), 7.78 (dd, J=13.6 Hz, J=1.6 Hz, 1H), 7.51 (d, J=9.2 Hz, 1H), 4.79 (m, 1H), 4.19 (t, J=9.2 Hz, 1H), 3.81 (m, 1H), 3.45 (t, J=5.2 Hz, 2H), 1.85 (s, 3H).

$^{13}$C-NMR (DMSO-d$_6$): δ 170.01, 166.15, 154.44, 153.96, 152.09, 150.53, 139.73, 138.82, 137.76, 130.56, 125.20, 123.95, 122.68, 119.46, 114.00, 106.18, 105.92, 71.80, 47.20, 41.35, 22.42.

ESI-MS m/z 440.2 (M+H+).

(5) Synthesis of Target Compound (S)—N-((3-(3-fluoro-4-(4-(pyridin-2-yl)-1H-pyrazol-1-yl)phenyl)-2-oxooxazolidin-5-yl)methyl)acetamide (13f)

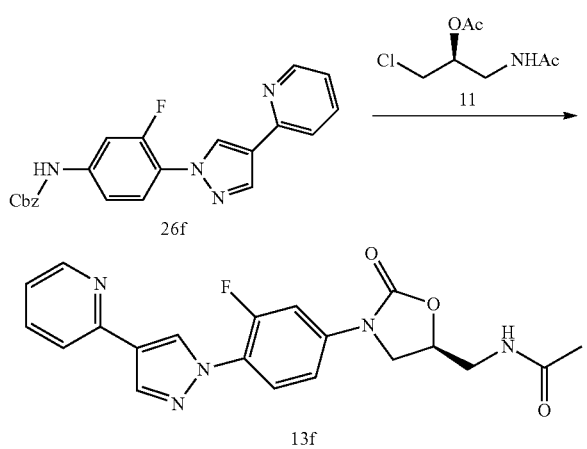

150 mg of compound 26f was dissolved in 10 mL anhydrous THF under nitrogen atmosphere. While the mixture was maintained in an ice-water bath, 154.1 mg of t-BuOLi was added under stirring for 5 minutes. Then, compound 11 (149.9 mg) was added into the resultant mixture, and then the ice-water bath was removed. The reactant was warmed to room temperature and reacted for 36 hours. After completion of the reaction, dichloromethane (10 mL), water (10 mL) and acetic acid (22 μL) were added into the reaction mixture, followed by stirring for another 1 minute. Then, the mixture was allowed to stand for separation. The aqueous phase was extracted with dichloromethane for three times. The combined organic phase was dried and then subjected to purification by column chromatography to get the product 13f as a white solid (58 mg), with a yield of 38.2%.

$^1$H-NMR (400 MHz, CDCl$_3$): δ 8.61 (d, J=4 Hz, 1H), 8.52 (d, J=6.8 Hz, 2.4H), 8.22 (s, 1H), 7.94 (t, J=8.8 Hz, 1H), 7.77-7.69 (m, 2H), 7.55 (d, J=8 Hz, 1H), 7.27-7.26 (m, 1H), 7.18-7.15 (m, 1H), 6.06 (t, J=6 Hz, 1H), 4.86-4.80 (m, 1H), 4.11 (t, J=9.2 Hz, 1H), 3.86-3.82 (m, 1H), 3.78-3.62 (m, 2H), 2.04 (s, 3H).

$^{13}$C-NMR (DMSO-d$_6$): δ 170.51, 154.47, 152.94, 151.26, 149.94, 139.70, 139.15, 137.43, 129.96, 125.61, 125.19, 123.42, 122.19, 120.38, 114.52, 106.68, 72.29, 47.70, 41.84, 22.91.

ESI-MSm/z 418.08 (M+Na+).

EXAMPLE 22

Synthesis of Target Compound (S)—N-((3-(3-fluoro-4-(5-(pyridin-3-yl)-1H-pyrazol-1-yl)phenyl)-2-oxooxazolidin-5-yl)methyl)acetamide (14a)

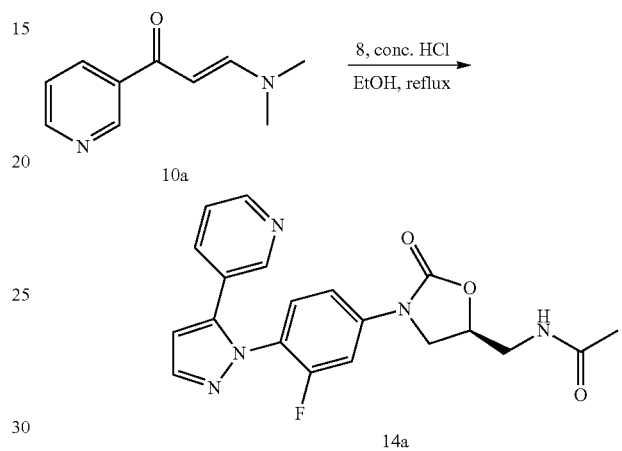

(E)-3-(dimethylamino)-1-(pyridin-3-yl)prop-2-en-1-one (58 mg, 0.327 mmol) and (S)—N-((3-(3-fluoro-4-hydrazinophenyl)-2-oxooxazolidin-5-yl)methyl)acetamide (94 mg, 0.327 mmol) were combined with a solvent, ethanol (3 mL), and then the mixture was slowly heated to reflux, followed by addition of concentrated hydrochloric acid (40 μL). The reaction mixture was maintained under reflux until completion of the reaction as monitored by TLC. Then, the reaction mixture was poured into water and then was extracted with dichloromethane. The dichloromethane layer was rotary evaporated. The residue was purified with column chromatography to afford 55 mg light yellow solid, with a yield of 40.7%, melting point: 83.7-85.9° C., HPLC: 98.2%.

$^1$H-NMR (400 MHz, CDCl$_3$): δ 8.54 (d, J=4.4 Hz, 1H), 8.49 (s, 1H), 7.80 (d, J=2 Hz, 1H), 7.52 (m, 4H), 7.26 (m, 1H), 6.61 (d, J=2 Hz, 1H), 6.08 (d, J=6 Hz, 1H), 4.81 (m, 1H), 4.06 (t, J=9.2 Hz, 1H), 3.79 (m, 1H), 3.69 (m, 2H), 2.03 (s, 3H).

$^{13}$C-NMR (DMSO-d$_6$): δ 169.96, 156.99, 154.53, 153.93, 149.32, 148.00, 141.12, 140.44, 134.89, 129.72, 125.73, 123.60, 122.20, 113.85, 107.49, 105.47, 71.80, 47.14, 41.32, 22.40.

ESI-MS m/z 418.2 (M+Na+).

EXAMPLE 23

Synthesis of Target Compounds 14b-j (1) Synthesis of Target Compound (S)—N-((3-(3-fluoro-4-(5-(6-bromopyridin-2-yl)-1H-pyrazol-1-yl)phenyl)-2-oxooxazolidin-5-yl)methyl)acetamide (14b)

Compound 14b was prepared by the same steps as those of 14a, in the form of a light yellow solid, yield: 47.3%, melting point: 90.5-92.3° C., HPLC: 98.8%.

¹H-NMR (400 MHz, CDCl₃): δ 7.34 (dd, J=8 Hz, J=1.6 Hz, 2H), 7.28 (m, 1H), 6.84 (d, J=2 Hz, 1H), 6.15 (s, 1H), 4.82 (t, J=3.2 Hz, 1H), 4.10 (t, J=8.8 Hz, 1H), 3.83 (m, 1H), 3.68 (m, 2H), 2.03 (s, 3H).
¹³C-NMR (DMSO-d₆): δ 170.10, 157.25, 154.80, 153.95, 148.85, 140.92, 140.36, 139.86, 128.89, 127.13, 123.78, 121.21, 113.40, 108.16, 105.14, 71.78, 7.14, 41.32, 22.40.
ESI-MS m/z 496.1 (M+Na⁺).

(2) Synthesis of Target Compound (S)—N-((3-(3-fluoro-4-(5-(p-tolyl)-1H-pyrazol-1-yl)phenyl)-2-oxooxazolidin-5-yl)methyl)acetamide (14c)

Compound 14c was prepared by the same steps as those of 14a, in the form of a light yellow solid, yield: 50.9%, melting point: 89.5-91.9° C., HPLC: 98.3%. ¹H-NMR (400 MHz, CDCl₃): δ 7.74 (d, J=2 Hz, 1H), 7.52 (dd, J=12 Hz, J=2.8 Hz, 1H), 7.43 (t, J=8.8 Hz, 1H), 7.24 (m, 1H), 7.09 (m, 4H), 6.50 (d, J=2 Hz, 1H), 6.24 (s, 1H), 4.78 (t, J=2.4 Hz, 1H), 4.05 (t, J=8.8 Hz, 1H), 3.79 (m, 1H), 3.66 (m, 2H), 2.32 (s, 3H), 2.02 (s, 3H).
¹³C-NMR (DMSO-d₆): δ 169.97, 157.21, 154.74, 153.94, 144.30, 140.72, 140.12, 137.89, 129.64, 129.19, 127.39, 126.77, 122.77, 113.70, 106.38, 105.59, 105.34, 71.79, 47.14, 41.33, 22.40, 20.68.
ESI-MS m/z 431.2 (M+Na⁺).

(3) Synthesis of Target Compound (S)—N-((3-(3-fluoro-4-(5-(4-bromophenyl)-1H-pyrazol-1-yl)phenyl)-2-oxooxazolidin-5-yl)methyl)acetamide (14d)

Compound 14d was prepared by the same steps as those of 14a, in the form of a light yellow solid, yield: 44.0%, melting point: 96.8-98.8° C., HPLC: 98.5%.
¹H-NMR (400 MHz, CDCl₃): δ 7.81 (s, 1H), 7.48 (m, 4H), 7.26 (m, 2H), 7.07 (m, 2H), 6.54 (d, J=1.6 Hz, 1H), 5.95 (d, J=6.4 Hz, 1H), 4.80 (m, 1H), 4.07 (m, 1H), 3.70 (m, 3H), 2.04 (s, 3H).
¹³C-NMR (DMSO-d₆): δ 169.97, 157.02, 154.56, 153.92, 143.09, 140.92, 140.28, 139.39, 131.72, 130.99, 129.60, 128.84, 121.86, 113.82, 107.04, 105.62, 105.37, 71.79, 47.14, 41.33, 22.40.
ESI-MS m/z 473.2 (M+H⁺).

(4) Synthesis of Target Compound (S)—N-((3-(3-fluoro-4-(5-(pyridin-2-yl)-1H-pyrazol-1-yl)phenyl)-2-oxooxazolidin-5-yl)methyl)acetamide (14e)

Compound 14e was prepared by the same steps as those of 14a, in the form of a brown yellow solid, yield: 31.1%, melting point: 79.9-82.1° C., HPLC: 98.1%.
¹H-NMR (400 MHz, CDCl₃):δ 8.44 (d, J=4.8 Hz, 1H), 7.78 (s, 1H), 7.67 (t, J=8 Hz, 1H), 7.56 (m, 2H), 7.39 (d, J=8 Hz, 1H), 7.21 (m, 2H), 6.81 (s, 1H), 6.30 (m, 1H), 4.80 (t, J=2.4 Hz, 1H), 4.08 (t, J=9.2 Hz, 1H), 3.81 (t, J=8.4 Hz, 1H), 3.66 (m, 2H), 2.02 (s, 3H).
¹³C-NMR (DMSO-d₆): δ 169.99, 153.97, 149.11, 148.42, 142.94, 140.65, 139.56, 137.07, 128.82, 124.14, 123.04, 122.23, 113.37, 107.69, 105.23, 104.97, 71.75, 47.18, 41.34, 22.41.
ESI-MS m/z 396.2 (M+H+).

(5) Synthesis of Target Compound (S)—N-((3-(3-fluoro-4-(5-(4-(methylthiophenyl)-1H-pyrazol-1-yl)phenyl)-2-oxooxazolidin-5-yl)methyl)acetamide (14f)

Compound 14f was prepared by the same steps as those of 14a, in the form of a light yellow solid, yield: 34.0%, melting point: 175.4-177.6° C., HPLC: 99.4%.
¹H-NMR (400 MHz, CDCl₃): δ 7.75 (s, 1H), 7.52 (dd, J=12 Hz, J=2 Hz, 1H), 7.44 (t, J=8.4 Hz, 1H), 7.26 (d, J=8.4 Hz, 1H), 7.13 (s, 4H), 6.51 (d, J=1.2 Hz, 1H), 6.22 (s, 1H), 4.79 (t, J=2.8 Hz, 1H), 4.06 (t, J=8.8 Hz, 1H), 3.79 (t, J=7.2 Hz, 1H), 3.71 (m, 1H), 3.60 (m, 1H), 2.46 (s, 3H), 2.02 (s, 3H).
¹³C-NMR (DMSO-d₆): δ 169.97, 157.18, 154.72, 153.93, 143.83, 140.79, 140.23, 140.13, 138.96, 129.64, 127.87, 125.69, 122.67, 113.75, 106.49, 105.62, 105.37, 71.80, 47.15, 41.33, 22.40, 14.14.
ESI-MS m/z 441.2 (M+H).

(6) Synthesis of Target Compound (S)—N-((3-(3-fluoro-4-(5-(5-bromopyridin-2-yl)-1H-pyrazol-1-yl)phenyl)-2-oxooxazolidin-5-yl)methyl)acetamide (14g)

Compound 14g was prepared by the same steps as those of 14a, in the form of a yellow solid, yield: 47.9%, melting point: 92.7-95.4° C., HPLC: 98.9%.
¹H-NMR (400 MHz, CDCl₃): δ 8.20 (d, J=2 Hz, 1H), 7.90 (d, J=2 Hz, 1H), 7.52 (m, 2H), 7.42 (m, 2H), 7.30 (d, J=8 Hz, 1H), 6.61 (d, J=2 Hz, 1H), 6.17 (s, 1H), 4.82 (t, J=2.8 Hz, 1H), 4.04 (t, J=8.8 Hz, 1H), 3.81 (t, J=7.6 Hz, 1H), 3.68 (m, 2H), 2.04 (s, 3H).
¹³C-NMR (DMSO-d₆): δ 169.97, 156.87, 154.41, 153.92, 148.65, 141.12, 140.55, 139.91, 138.05, 129.66, 128.02, 125.46, 121.78, 113.92, 107.87, 105.54, 71.81, 47.14, 41.34, 22.40.
ESI-MS m/z 496.0 (M+Na⁺).

(7) Synthesis of Target Compound (S)—N-((3-(3-fluoro-4-(5-(pyridin-4-yl)-1H-pyrazol-1-yl)phenyl)-2-oxooxazolidin-5-yl)methyl)acetamide (14h)

Compound 14h was prepared by the same steps as those of 14a, in the form of a yellow solid, yield: 32.1%, melting point: 74.5-76.3° C., HPLC: 98.7%.
¹H-NMR (400 MHz, CDCl₃): δ 8.54 (d, J=5.2 Hz, 2H), 7.80 (d, J=2 Hz, 1H), 7.49 (m, 2H), 7.33 (dd, J=2.4 Hz, J=0.8 Hz, 1H), 7.12 (d, J=6 Hz, 2H), 6.67 (d, J=1.6 Hz, 1H), 6.22 (s, 1H), 4.81 (m, 1H), 4.08 (t, J=9.2 Hz, 1H), 3.82 (m, 1H), 3.64 (m, 2H), 2.03 (s, 3H).
¹³C-NMR (DMSO-d₆): δ 169.98, 156.98, 154.52, 153.94, 150.05, 141.56, 141.16, 140.55, 136.73, 129.49, 122.16, 121.50, 113.92, 108.10, 105.53, 71.83, 47.16, 41.33, 22.40, 18.61.
ESI-MS m/z 396.1 (M+H+).

(8) Synthesis of Target Compound (S)—N-((3-(3-fluoro-4-(5-(4-fluorophenyl)-1H-pyrazol-1-yl)phenyl)-2-oxooxazolidin-5-yl)methyl)acetamide (14i)

Compound 14i was prepared by the same steps as those of 14a, in the form of a yellow solid, yield: 42.2%, melting point: 111.4-112.9° C., HPLC: 98.5%.
¹H-NMR (400 MHz CDCl₃): δ 7.75 (d, J=2 Hz, 1H), 7.51 (dd, J=12 Hz, J=2.4 Hz, 1H), 7.45 (t, J=8.4 Hz, 1H), 7.25 (m, 1H), 7.19 (m, 2H), 6.98 (t, J=8.4 Hz, 2H), 6.50 (d, J=2 Hz, 1H), 6.03 (t, J=6 Hz, 1H), 4.80 (m, 1H), 4.06 (t, J=8.8 Hz, 1H), 3.71 (m, 3H), 2.03 (s, 3H).
¹³C-NMR (DMSO-d₆): δ 169.98, 163.16, 157.10, 154.64, 153.93, 143.28, 140.78, 140.23, 129.80, 129.65, 126.17, 122.43, 115.66, 113.75, 106.84, 105.58, 105.33, 71.80, 47.14, 41.32, 22.39.
ESI-MS m/z 435.1 (M+Na⁺).

(9) Synthesis of Target Compound (S)—N-((3-(3-fluoro-4-(5-(3,4-dimethoxyphenyl)-1H-pyrazol-1-yl)phenyl)-2-oxooxazolidin-5-yl)methyl)acetamide (14j)

Compound 14j was prepared by the same steps as those of 14a, in the form of a yellow solid, yield: 42.6%, melting point: 153.7-156.1° C., HPLC: 98.3%.

$^1$H-NMR (400 MHz CDCl$_3$): δ 7.74 (d, J=1.6 Hz, 1H), 7.52 (dd, J=12 Hz, J=2.4 Hz, 1H), 7.43 (t, J=8.4 Hz, 1H), 7.25 (dd, J=9.6 Hz, J=2.4 Hz, 1H), 6.75 (m, 3H), 6.49 (d, J=2 Hz, 1H), 6.19 (t, J=8.4 Hz, 1H), 4.79 (m, 1H), 4.05 (t, J=9.2 Hz, 1H), 3.86 (s, 3H), 3.79 (m, 1H), 3.69 (m, 4H), 3.62 (m, 1H), 2.02 (s, 3H).

$^{13}$C-NMR (DMSO-d$_6$): δ 169.98, 157.44, 154.97, 153.95, 148.84, 148.37, 144.31, 140.59, 140.16, 129.82, 122.93, 121.98, 120.05, 113.72, 111.45, 106.65, 105.65, 105.40, 71.80, 55.34, 47.18, 41.33, 22.38.

ESI-MS m/z 477.1 (M+Na$^+$).

EXAMPLE 24

Preparation of Hydrochloride Salt of Compound 12a

Accurately weighed 2.5 g of Compound 12a was placed into a round-bottom flask (250 ml), and was completely dissolved with acetone (100 mL). Then, diethyl ether solution saturated with HCl was slowly dropped to the flask until no significant increase of white precipitate. Thus obtained mixture was stirred for another 30 minutes at room temperature and then filtered in vacuum. The filter cake was dried to afford the hydrochloride salt (2.41 g) as a light yellow solid, with a yield of 88.3%.

EXAMPLE 25

Assay for In Vitro Antibacterial Activity of the Oxazolidinone Compounds Against *Staphylococcus Aureus*

1. Test Materials

Strains: strain ATCC25923 is available from the American Type Culture Collection, and is used as a standard strain of *Staphylococcus Aureus;*

Liquid medium: MH bouillon culture medium, a product of BD Company, United States of American;

Tested Compounds: compounds 12a, 13 and 14 prepared according to the methods above, and Linezolid purchased from Pfizer.

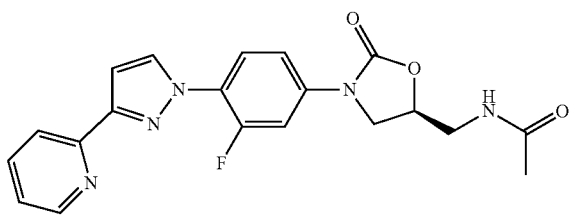

12a

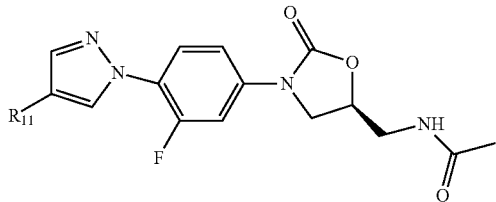

13

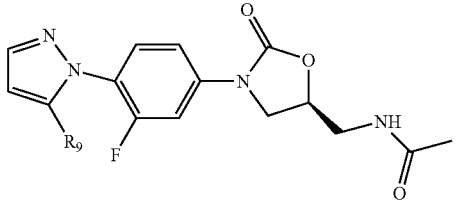

14

2. Assaying Methodology (1) Preparation of Test Strain:

The test strain was inoculated into the liquid medium and cultured at 37° C. for 16-18 h. The culture liquid and MH medium were put into two blank wells of a 96-well plate, respectively. Then, the absorptions thereof were measured by a Microplate reader. The difference between the absorption values of the culture liquid and MH medium is the adsorption of the bacteria. The concentration of the culture liquid can be calculated according to the formula of 1OD=50 million CFU/mL. The culture liquid was diluted with the MH bouillon culture medium to 5000 CFU/mL for further use.

(2) Preparation of Tested Compounds:

Compounds 12a, 13 and 14 were dissolved in DMSO to 1 mg/mL, and then filtered with a 0.22 μm filter to obtain the compound solutions. And then they were gradually diluted to a desired concentration (10× final concentration) with the liquid medium, so as to obtain a series of dilutions. The final concentration grade of the dilutions of each tested compound consists of 14 concentrations, which includes: 0.03125 μg/mL, 0.0625 g/mL, 0.125 μg/mL, 0.25 μg/mL, 0.51 μg/mL, 1 μg/mL, 2 μg/mL, 4 μg/mL, 8 μg/mL, 16 μg/mL, 32 μg/mL, 64 μg/mL, 128 μg/mL and 256 μg/mL.

(3) Assaying Procedures:

10 μL of each of the compound dilutions above was added into a well of a 96-well plate. 90 μL of the culture liquid (5000 CFU/mL) was added into each of the wells, respectively, mixed with the dilutions to render the tested compound concentration to the final concentration. The resulted mixture was incubated at 37° C. for 16-18 h, and then the OD$_{630}$ thereof was measured. A culture liquid free of the tested compounds is used as a blank control, and three parallel tests with the same concentration of each compound were performed. The minimum inhibitory concentration (MIC) of each compound on the standard strain of *Staphylococcus Aureus* and other test strains was determined. Specifically, among the culture liquid contained in the wells of the microplate, the first three lowest concentrations under which growth of the test strains could be observed were chose for further evaluation of the MIC. A culture liquid free of tested compounds was used as a blank control. Each of the culture liquids was homogenized independently, and then was diluted with a sterile saline. Each of the diluted culture liquids was plated onto a MH bouillon plate and incubated at 37° C. for 20 h in incubator. After the incubation, the number of the colonies on each plate was counted. As compared with the blank control group, the lowest concentration of each of the test compound groups, at which 80% reduction in the colony number of the strains was achieved, was recorded as the MIC.

3. Results

TABLE 2

The MIC (μg/mL) of test compounds in-vitro inhibiting *S. aureus*, *S. pneumoniae*, *S. agalactiae* and *E. faecalis*

| Compound | Substituent | S. aureus (12 strains) | S. pneumoniae (10 strains) | S. agalactiae (5 strains) | E. faecalis (7 strains) |
|---|---|---|---|---|---|
| 13a | $R_{11}$ is 4-pyridyl | 0.5-16 | 0.125-16 | 0.25-16 | 0.25-16 |
| 13b | $R_{11}$ is 4-methylphenyl | 1-8 | 0.5-8 | 0.25-8 | 0.5-8 |
| 13c | $R_{11}$ is 4-methoxyphenyl | 1-8 | 0.5-8 | 0.5-8 | 0.25-8 |
| 13d | $R_{11}$ is 4-chlorphenyl | 1-4 | 0.25-4 | 0.5-8 | 0.5-8 |
| 13e | $R_{11}$ is 5-carboxyl--2-pyridyl | 1-8 | 0.5-8 | 0.5-4 | 1-8 |
| 13f | $R_{11}$ is 2-pyridyl | 0.25-2 | 0.25-1 | 0.25-2 | 0.5-2 |
| 14a | R9 is 3-pyridyl | 2-16 | 1-16 | 2-16 | 2-16 |
| 14b | $R_9$ is 2-bromine-6-pyridyl | 4-32 | 2-32 | 4-32 | 4-32 |
| 14c | $R_9$ is 4-methylphenyl | 4-32 | 2-16 | 2-32 | 2-32 |
| 14d | $R_9$ is 4-brominephenyl | 2-16 | 1-8 | 2-16 | 2-16 |
| 14e | $R_9$ is 2-pyridyl | 0.5-16 | 0.125-16 | 0.25-16 | 0.25-16 |
| 14f | $R_9$ is 4-methylmercaptophenyl | 1-8 | 0.5-8 | 0.25-8 | 0.5-8 |
| 14g | $R_9$ is 5-bromine-2-pyridyl | 1-8 | 0.5-8 | 0.5-8 | 0.25-8 |
| 14h | $R_9$ is 4-pyridyl | 1-4 | 0.25-4 | 0.5-8 | 0.5-8 |
| 14i | $R_9$ is 4-fluorine phenyl | 1-8 | 0.5-8 | 0.5-4 | 1-8 |
| 14j | $R_9$ is 3,4-dimethoxy phenyl | 0.25-2 | 0.25-1 | 0.25-2 | 0.5-2 |
| 12a | $R_{10}$ is 2-pyridyl | 2-16 | 1-16 | 2-16 | 2-16 |
| Linezolid | — | 4-32 | 2-32 | 4-32 | 4-32 |

As shown in Table 2, the novel oxazolidinone compounds 12, 13 and 14 exhibit inhibitory activity on *S. aureus*, *S. pneumoniae*, *S. agalactiae* and *E. faecalis*, and bring forth an optimistic prospect for development of the novel compounds into a pharmaceutical composition. It also shows that Compound 13f has the most optimum activity.

EXAMPLE 26

Determination of the In Vitro Inhibitory Activity of Compound 13f Against Gram-Positive Bacteria In order to further study the antibacterial spectrum of Compound 13f, we tested in vitro inhibitory activity of compound 13f on 120 strains of gram-positive bacteria established by clinical isolation, and the MIC values were shown in Table 3.

In order to investigate whether the antibacterial activity of Compound 13f is bacteriostatic or bactericidal to gram-positive bacteria, we tested its MBC on 10 strains of gram-positive bacteria (established by clinical isolation), results as shown in Table 4.

1. Test Materials (1) Strains:

Standard strains, including *Staphylococcus aureus* ATCC29213, *S. pneumoniae* ATCC49619, *E. faecalis* ATCC29212, are all available from the American Type Culture Collection.

Clinically isolated strains: There are total 120 clinical strains of gram-positive bacterium including: 37 strains of *Staphylococcus aureus* (consisting of 14 strains of methicillin sensitive *Staphylococcus aureus* MSSA and 23 strains of methicillin resistant *Staphylococcus aureus* MRSA); 27 strains of *Streptococcus pneumoniae* (consisting of 13 strains of penicillin sensitive *Streptococcus pneumoniae* PSSP and 14 strains of penicillin insensitive or resistant *Streptococcus pneumoniae* PISP+PRSP); 15 strains of *Streptococcus pyogenes*; 17 strains of *Streptococcus agalactiae*; 24 stains of *Enterococcus faecium* (consisting of 12 strains of vancomycin sensitive *Enterococcus faecium* and 12 strains of vancomycin resistant *Enterococcus faecium*).

(2) Tested compounds: Compound 13f was prepared by the methods above, with potency of over 98%; Linezolid was purchased from Pfizer, with potency of 100%.

2. Test Method (1) Preparation of Test Strains:

*Staphylococcus* and *Enterococcus faecium* were incubated in Mueller-Hinton agar medium (MHA medium) at 35° C. for 16-20 h; *S. pneumoniae* was incubated in Cation-Adjusted Mueller-Hinton Broth medium (CAMHB medium) supplemented with 2.5-5.5% (v/v) lysed horse blood (LHB) at 35° C. for 20-24 h; and *Streptococcus* were incubated in sheep blood-containing medium (prepared by addition of 5% defibrinated sheep blood into MHA media) at 35° C. for 20-24 h in 5% $CO_2$ environment ($CO_2$ incubator). Before test of the compound activity, each stock of the bacteria strains was activated and colonized in the following manner: the stock was transferred and cultured in a liquid culture medium, the culture liquid was smeared onto an agar plate with an inoculating loop to obtain bacterial colonies on the plate after incubation, and then a colony of the bacteria was chose to be suspended into the liquid culture medium for performing the test of compound activity. As a result, fresh bacteria cells were applied to the test. The standard strains were used as sensitive bacterium to control the quality of the experiments, and a plate or tube containing no antibacterial compounds is used as a blank control for the growth of test strains.

(2) Determination of MIC

The minimal inhibitory concentration (MIC) of the test compounds on the strains of *Streptococcus pneumoniae* was determined by a standard broth macrodilution method, while the MIC of the test compounds on the other bacteria stains was determined by standard agar double dilution methods. The concentration of the test compounds was in the range of 32 mg/L-0.016 mg/L. The bacterial suspensions to be tested were inoculated by a multipoint inoculator, and the inoculation amount at each point is $10^4$ CFU. The MIC of the test compound to each strain of the bacteria was determined.

(3) Minimum Bactericidal Concentration (MBC) Test

The MBC was determined by a tube double dilution method. Solutions of the test compounds was prepared and serially diluted. Each of the solutions was mixed with a bacterium suspension ($10^6$ CFU/mL), and then was incubated at 35° C. overnight. 0.1 mL of the culture supernatant of each tubes was inoculated on a plate containing no antibiotics, and then incubated at 35° C. for 18 h. The lowest concentration of the compound at which the colony number observed on the plate was less than 50 was regard as the MBC.

3. Result

TABLE 3

The MIC of compound 13f against 120 strains of clinically isolated gram-positive bacterium

| Number of strain | compounds | MIC (µg/L) | | | |
|---|---|---|---|---|---|
| | | $MIC_{50}$ | $MIC_{90}$ | $MIC_{mode}$ | $MIC_{range}$ |
| MSSA (14 strains) | 13f | 1 | 1 | 1 | 0.5-1 |
| | Linezolid | 1 | 1 | 1 | 1 |
| MRSA (23 strains) | 13f | 1 | 1 | 1 | 0.5-1 |
| | Linezolid | 1 | 1 | 1 | 0.5-1 |
| PSSP[a] (13 grains) | 13f | 1 | 1 | 1 | 0.5-1 |
| | Linezolid | 1 | 1 | 1 | 0.5-1 |
| PNSP[a] (14 grains) | 13f | 0.5 | 1 | 0.5 | 0.5-1 |
| | Linezolid | 0.5 | 1 | 0.5 | 0.5-1 |
| Streptococcus pyogenes (15 strains) | 13f | 0.25 | 0.5 | 0.25 | 0.25-0.5 |
| | Linezolid | 0.25 | 1 | 0.25 | 0.25-1 |
| Streptococcus agalactiae (17 strains) | 13f | 1 | 1 | 1 | 0.5-1 |
| | Linezolid | 1 | 1 | 1 | 0.5-1 |
| Enterococcus faecium-sensitive vancomycin (12 strains) | 13f | 1 | 1 | 1 | 1-2 |
| | Linezolid | 1 | 1 | 1 | 1-2 |
| Enterococcus faecium-resistant vancomycin (12 strains) | 13f | 1 | 1 | 1 | 1-2 |
| | Linezolid | 1 | 1 | 1 | 1-2 |

[a]The criterion for the judgment against PSSP was: penicillin MIC ≤0.062 µg/L.

As shown in Table 3, the antibacterial activity of test compound 13f on test strains is almost the same with that of Linezolid. Compound 13f has excellent antibacterial effect on gram-positive bacteria, including MRSA and VRE.

TABLE 4

The MBC of compound 13f against 10 strains of clinically isolated gram-positive bacteria

| No. of strains | species of bacteria | MIC value (µg/L) | MBC value (µg/L) | MBC/MIC |
|---|---|---|---|---|
| 09U035 | MSSA | 2 | 2 | 1 |
| 09O077 | MSSA | 1 | 2 | 2 |
| 09L075 | MRSA | 2 | 4 | 2 |
| 09N120 | MRSA | 2 | 2 | 1 |
| 09G343 | PSSP | 0.5 | 1 | 2 |
| 09J699 | PNSSP | 1 | 2 | 2 |
| 09D263 | VSE | 4 | 8 | 2 |
| 09H202 | VSE | 4 | 8 | 2 |
| 09ZB145 | VRE | 4 | 8 | 2 |
| 09ZB137 | VRE | 4 | 8 | 2 |

The results of MBC test showed that the ratio of MBC/MIC of compound 13f against all the 10 tested strains was ≤4, indicating a bactericidal effect. Besides, the ratio of MBC/MIC of compound 13f on Staphylococcus sp. and Streptococcus pneumoniae was 1-2, showing a more significant bactericidal effect. As to the bactericidal effect on E. faecalis, the compound exhibited a weaker effect than that on Staphylococcus sp., because among 4 tested strains of E. faecalis, each of the MBC/MIC ratio of 3 strains was 4.

EXAMPLE 27

Experiment of In Vivo Activity of Compound 13f in a Mouse Model of Systemic Infection, Using Linezolid as a Control 1. Materials and Agents Animal model: SPF grade C57 mice, 4-6 weeks age, weight 18-22 g, ten mice per group;

Infectious strain: ATCC 25923, grown in a MHB medium to a period of logarithmic growth;

Test compounds: Compound 13f prepared according to the methods above, and Linezolid as a control, purchased from Airsea Pharmaceutical Ltd., (Taizhou, ZheJiang Province, China;

Formulation and dosage of the test compounds: To evaluate the treating effect of compound 13f, an animal model of intraperitoneal infection by bacteria was established and grouped into 13f group and Linezolid group. The same dosage of the compound 13f and Linezolid was administrated to the groups, respectively.

2. Test Method (1) Infection Dosage and Route:

The minimum lethal dose (MLD) was determined as follows: Bacterial stock liquid cultured overnight was adjusted to 0.5 McFarland with saline solution, and subsequently subjected to a proper serial dilution. 3-5 dilutions with different concentrations of the bacteria were used to infect mice (10 mice per concentration), respectively, by intraperitoneal injection with a volume of 0.5 mL of the dilution. The minimum concentration at which 100% mice were dead was regarded as MLD. For purpose of ensuring experimental reliability, two control groups (MLD control group and 1/10MLD control group) were used in this experiment. The mortality of the MLD control group was 100%, while the mortality of the 1/10OMLD control group was 30%. The morality results of these two controls indicated that the infection dosage was appropriate and the experiment was reliable. To enhance virulence of the infectious bacteria, 15% yeast was added into the bacterial liquid for infection. The result obtained in the preliminary test suggested that the MLD of ATCC 25923 on C57 mouse was 0.2OD bacteria+15% yeast.

(2) Test Procedure

Experimental animal and grouping: SPF grade C57 mice (purchased from Experiment Animal Center, West China Hospital of Sichuan University), 4-6 weeks old, weighting 18-22 g, were randomly divided into groups, including model group, and treating groups consisting of group administrated with compound 13f at 5 mg/kg, group administrated with compound 13f at 10 mg/kg, group administrated with Linezolid at 5 mg/kg and group administrated with Linezolid at 10 mg/kg, with ten mice per group.

1) Based on the MLD result from the preliminary experiment, the mice were infected by intraperitoneal injection with a saline suspension of ATCC 25923, containing 15% yeast. Injection dosage of the bacteria was 0.2 OD/mice.

2) Administration time and frequency: The above mentioned compounds (compound 13f and Linezolid) were administrated to the mice of the treating groups 1 hour before and 4 hour after the infection, respectively. Meanwhile, the mice of the model group received only solvents in the same volume as that of the compound solution administered in the treating group. The treating groups includes compound 13f group at 10 mg/kg, compound 13f group at 5 mg/kg, Linezolid group at 10 mg/kg and Linezolid group at 5 mg/kg.

3) Administration route: intravenous injection;

4) Dissolving compounds: The compounds were dissolved with 30% water solution of hydroxypropyl-β-cyclodextrin;

5) Efficacy observation: After infection and administration, the appetites, activities, symptoms and signs of the test mice were observed regularly. The survival rate was monitored every 4 h. The observation lasted for 7 days. During this period of observation, dissection of dying mice was immediately carried out after their death, and a histopathological examination was conducted, if necessary.

6) Evaluation: Main indexes include survival time, survival rate, and CFU count of organ and blood.

3. Results

In this test, two dosages 10 mg/kg and 5 mg/kg of each compound were administrated to the treating groups of mice, respectively, and the mortality was used to evaluate the in vivo effect of compound 13f and compare with that of Linezolid.

FIG. 1 showed the in vivo effect of compound 13f at the dosage of 10 mg/kg. Death of mice was observed in model group after 4 h of infection, and the mortality reached 80% in 24 h, 90% in 48 h and 100% in 72 h. All the 10 mice in the Linezolid group survived, so the protection rate is 100%. The survival rate of compound 13f group is 100%, showing the same therapeutic effect as linezolid.

Figure 2:
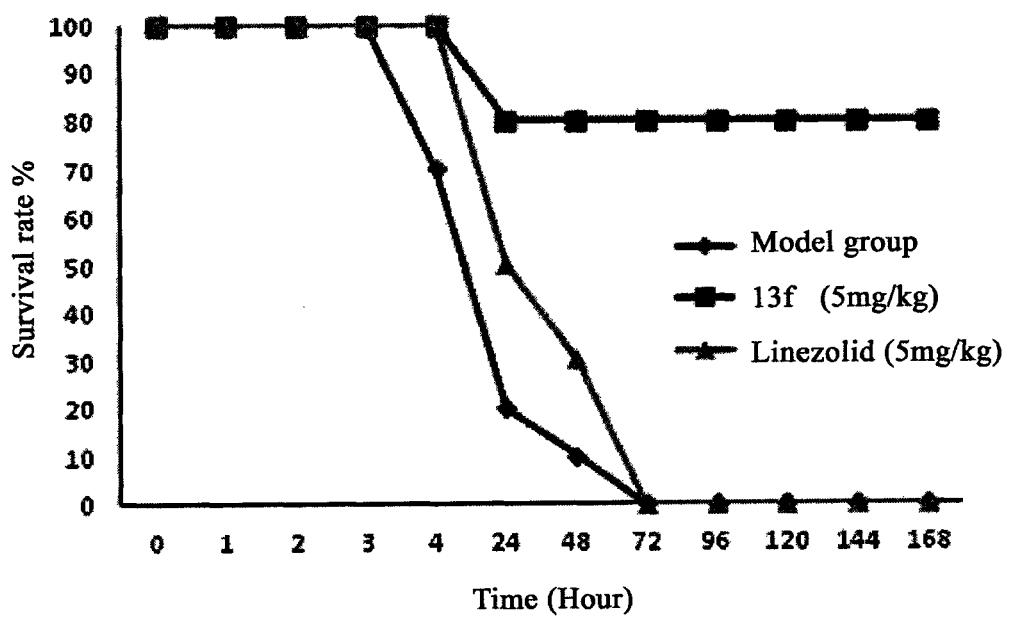
FIG. 2 shows the test result of the group with a dosage of 5 mg/kg.

FIG. 2 showed the in vivo effect of compound 13f at the dosage of 5 mg/kg. Death of the mice in model group was observed after 4 h of infection, and the mortality reached 80% in 24 h, 90% in 48 h and 100% in 72 h. Death of mice in linezolid group was observed after 5 h of infection, and the mortality reached 50% in 24 h, 70% in 48 h and 100% in 72 h. Death of mice in compound 13f group was also observed after 5 h of infection, but the mortality only reached 20% in 24 h. Then, the survival rate remained until the end of the experiment, which indicated that compound 13f at the dosage of 5 mg/kg had better in vivo treatment effect and protection effect in a mouse model of systemic bacterial infection than that of Linezolid.

EXAMPLE 28

Cytotoxicity Experiment of the Novel Oxazolidinone Compounds (1) Inoculating cells: Experimental cells in the growth of logarithmic phase were collected and suspended. The cell concentration of the suspension was adjusted so that they could be inoculated into the wells of 96-well micro plate at a density between $10^3$-$10^4$ cells per well (200 μl per well).

(2) Culturing cells: The cells were cultured at normal conditions for 3 days and then exposed to 50 uM compounds for test.

(3) Coloring reaction: At 24 h, 48 h and 72 h after the cells being exposed to the compounds for test, 200 μl culture medium containing 20 μl MTT solution (5 mg/ml) was added into each well, and the well was further incubated at 37° C. for 2 hours to terminate the incubation. After the incubation, the supernatants were removed from the wells. In the event there were suspended cells in the wells, centrifugation should be performed before removal of supernatant from the wells. After the removal, 150 μl DMSO was added to each well and mixed thoroughly by agitation for 10 mins to fully dissolve crystals.

(4) Ascertainment of colorimetry: The absorbance value at 490 nm of each well was determined by Enzyme-linked immunosorbent Monitor. The growth curve of the experimental cells was plotted by taking time as x-coordinate and absorbance value as y-coordinate. In addition, an inhibition ratio could be calculated in accordance with the following formula:

Inhibition ratio=(absorbance value of control group-absorbance value of administering group)/absorbance value of control group×100%.

(5) Experiment results: The results were shown in Table 5.

TABLE 5

Inhibition ratio of the novel oxazolidinone compounds (50 uM) on normal cells (48 h)

| Compound | Substituent | HEK-293 | L-02 |
|---|---|---|---|
| 13a | $R_{11}$ is 4-pyridyl | 11% | 4% |
| 13b | $R_{11}$ is 4-methylphenyl | 12% | 5.58% |
| 13c | $R_{11}$ is 4-methoxyphenyl | 32% | 10.36% |
| 13d | $R_{11}$ is 4-chlorphenyl | 21% | 39.34% |
| 13e | $R_{11}$ is 5-carboxyl--2-pyridyl | 36.3% | 38% |
| 13f | $R_{11}$ is 2-pyridyl | 2.7% | 2.74% |
| 14a | $R_9$ is 3-pyridyl | 14% | 7.51% |
| | | | 10.36% |
| 14b | $R_9$ is 2-bromine-6-pyridyl | 19.5% | 21% |
| 14c | $R_9$ is 4-methylphenyl | 40% | 39% |
| 14d | $R_9$ is 4-brominephenyl | 55% | 39% |
| 14e | $R_9$ is 2-pyridyl | 47% | 39% |
| 14f | $R_9$ is 4-methylmercaptophenyl | 40% | 29% |
| 14g | $R_9$ is 5-bromine-2-pyridyl | 10% | 5.9% |
| 14h | $R_9$ is 4-pyridyl | 5% | 14% |
| 14i | $R_9$ is 4-fluorine phenyl | 5.5% | 9% |
| 14j | $R_9$ is 3,4-dimethoxy phenyl | 7% | 12% |
| 0.30 acres | $R_{10}$ is 2-pyridyl | 5.5% | 20% |
| Linezolid | — | >50% | >50% |

As shown in Table 5, the novel oxazolidinone compounds of the present invention have less cytotoxicity than that of the commercial Linezolid. These data also suggest that the novel oxazolidinone compounds of the present invention are prospective to be developed into a medicine which is more clinically tolerable than Linezolid.

The invention claimed is:

1. An oxazolidinone compound or its pharmaceutically acceptable salt, wherein the compound has a structure represented by Formula I:

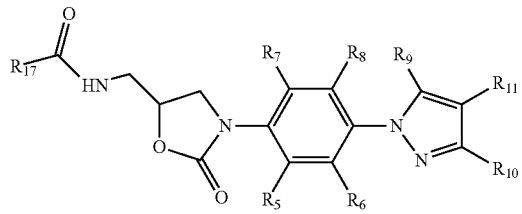

Formula I wherein:
$R_5$ to $R_8$ are each independently H, F, Cl, Br or $C_1$-$C_8$ alkyl;
$R_9$, $R_{10}$ and $R_{11}$ are each independently H,

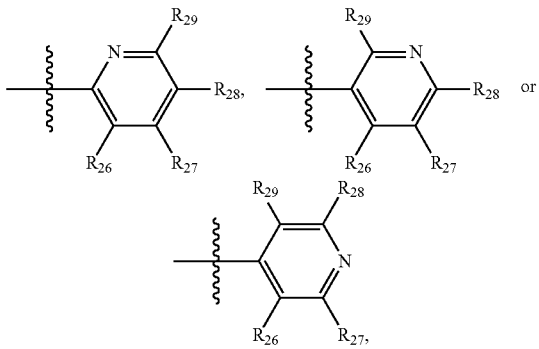

and at least one of $R_9$, $R_{10}$ and $R_{11}$ is not H;
$R_{17}$ is H or $C_1$-$C_4$ alkyl; and
$R_{26}$ to $R_{29}$ are each independently H, $C_1$-$C_4$ alkyl, halogen or carboxyl.

2. The oxazolidinone compound or its pharmaceutically acceptable salt according to claim 1, wherein:
$R_5$ to $R_8$ are each independently H, F, Cl, Br or $C_1$-$C_4$ alkyl; and
$R_{26}$ to $R_{29}$ are each independently H, $C_1$-$C_4$ alkyl, F, Cl, Br or carboxyl.

3. The oxazolidinone compound or its pharmaceutically acceptable salt according to claim 2, wherein:
$R_5$ to $R_8$ are each independently H, F, Cl, or Br; and
$R_{26}$ to $R_{29}$ are each independently H, F, Cl, or Br.

4. The oxazolidinone compound or its pharmaceutically acceptable salt according to claim 1, wherein:
$R_{17}$ is methyl group and the compound has the structure represented by Formula II:

Formula II

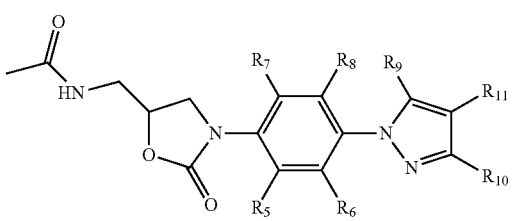

wherein:
$R_9$ and $R_{10}$ are each independently H;
$R_{11}$ is

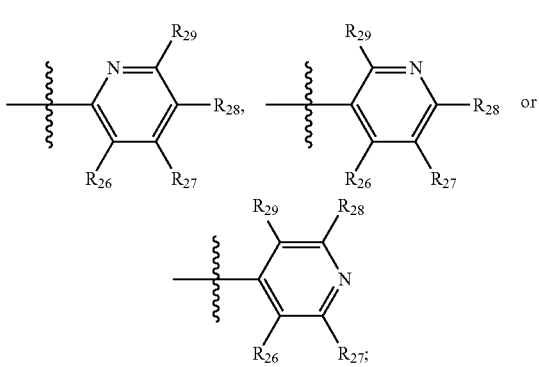

and
$R_{26}$ to $R_{29}$ are H.

5. The oxazolidinone compound or its pharmaceutically acceptable salt according to claim 4, wherein:
$R_{11}$ is

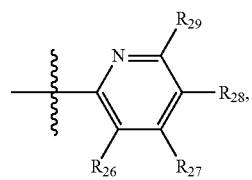

such that the compound has the structure represented by Formula III:

Formula III

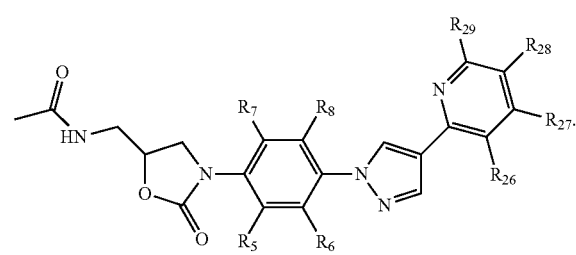

6. The oxazolidinone compound or its pharmaceutically acceptable salt according to claim 1, wherein:
$R_{17}$ is methyl; $R_5$, $R_6$ and $R_7$ are H; and $R_8$ is F; such that the compound has the structure represented by Formula IV:

Formula IV

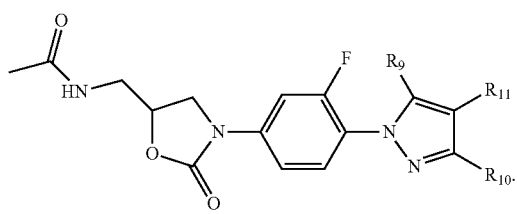

7. The oxazolidinone compound or its pharmaceutically acceptable salt according to claim 6, wherein:
$R_9$ and $R_{10}$ are H, and the compound has the structure represented by Formula V:

Formula V

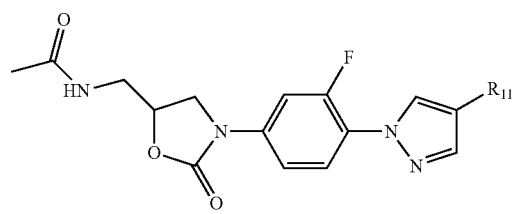

wherein R₁₁ is

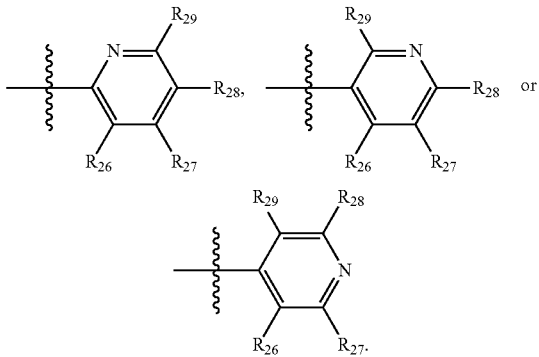

8. The oxazolidinone compound or its pharmaceutically acceptable salt according to claim 6, wherein, the structure of the compound is

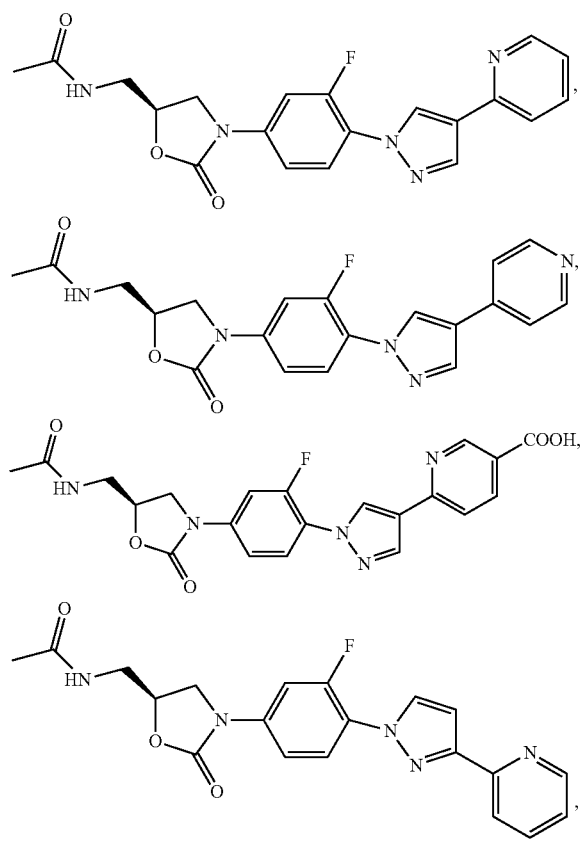

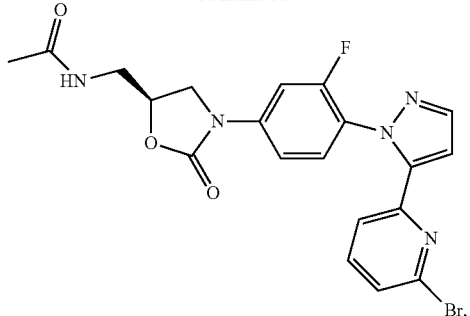

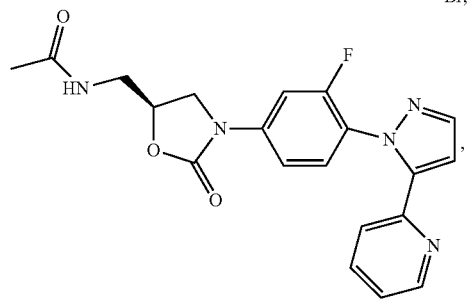

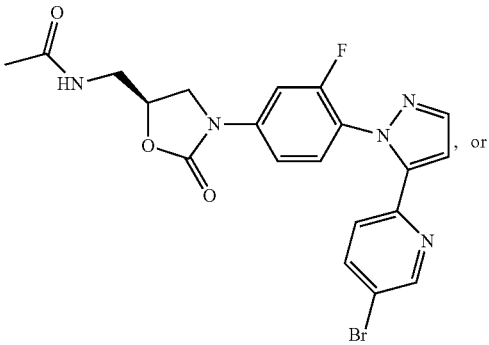

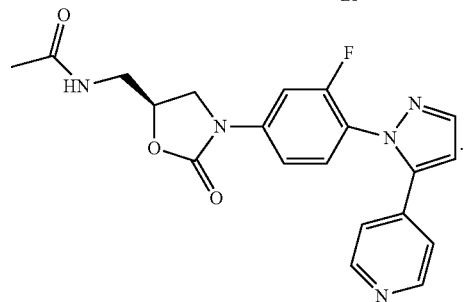

9. The oxazolidinone compound or its pharmaceutically acceptable salt according to claim 1, wherein the pharmaceutically acceptable salt is prepared from the oxazolidinone compound with hydrochloric acid, hydrobromic acid, hydrofluoric acid, sulfuric acid, phosphoric acid, nitric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, ethanesulfonic acid, isethionic acid, p-toluenesulfonic acid, benzenesulfonic acid, naphthalenesulfonic acid, trifluoro acetic acid or aspartic acid.

10. The oxazolidinone compound or its pharmaceutically acceptable salt according to claim 9, wherein the pharmaceutically acceptable salt is hydrochloride or mesylate salt of the oxazolidinone compound.

11. A method of preparing an antibiotic medicine comprising the step of combining the oxazolidinone compound or its pharmaceutically acceptable salt according to claim 1 with at least one pharmaceutically acceptable auxiliary ingredient.

12. A pharmaceutical composition, comprising an effective amount of the oxazolidinone compound or its pharmaceutically acceptable salt according to claim 1 and a pharmaceutically acceptable auxiliary ingredient or ingredients.

13. The pharmaceutical composition according to claim 12, wherein the composition is in a form of oral formulation, injection formulation or liniment.

* * * * *